United States Patent
Margolis

(10) Patent No.: US 7,704,216 B2
(45) Date of Patent: Apr. 27, 2010

(54) METHOD FOR ASSESSING THE ACCURACY OF TEST RESULTS

(75) Inventor: Robert Margolis, Arden Hills, MN (US)

(73) Assignee: Audiology Incorporated, Arden Hills, MN (US)

( * ) Notice: Subject to any disclaimer, the term of this patent is extended or adjusted under 35 U.S.C. 154(b) by 1191 days.

(21) Appl. No.: 11/210,396

(22) Filed: Aug. 24, 2005

(65) Prior Publication Data

US 2007/0179398 A1      Aug. 2, 2007

(51) Int. Cl.
*A61B 5/00*     (2006.01)
*H04R 29/00*    (2006.01)

(52) U.S. Cl. .................. 600/559; 600/300; 381/58; 381/60

(58) Field of Classification Search ............ 600/300, 600/559; 381/58, 60
See application file for complete search history.

(56) References Cited

U.S. PATENT DOCUMENTS

| | | | |
|---|---|---|---|
| 4,275,744 A | 6/1981 | Thornton et al. | |
| 4,462,411 A | 7/1984 | Rickards | |
| 4,862,505 A | 8/1989 | Keith et al. | |
| 4,926,969 A | 5/1990 | Wright et al. | |
| 5,023,783 A | 6/1991 | Cohen et al. | |
| 5,083,571 A | 1/1992 | Prichep | |
| 5,197,332 A | 3/1993 | Shennib | |
| 5,282,475 A | 2/1994 | Urbach et al. | |
| 5,697,379 A | 12/1997 | Neely et al. | |
| 5,788,648 A | 8/1998 | Nadel | |
| 5,811,681 A | 9/1998 | Braun et al. | |
| 5,833,626 A | 11/1998 | Leysieffer | |
| 6,071,246 A | 6/2000 | Sturzebecher et al. | |
| 6,167,138 A | 12/2000 | Shennib | |
| 6,196,977 B1 | 3/2001 | Sininger et al. | |
| 6,200,273 B1 | 3/2001 | Sininger et al. | |
| 6,343,230 B1 | 1/2002 | Smits et al. | |
| 6,484,010 B1 | 11/2002 | Sheehan | |
| 6,496,585 B1 * | 12/2002 | Margolis | 381/60 |
| 6,503,207 B2 | 1/2003 | Stone | |
| 6,547,746 B1 | 4/2003 | Marino | |
| 6,602,202 B2 | 8/2003 | John et al. | |
| 6,620,100 B2 | 9/2003 | Smits et al. | |
| 6,644,120 B1 | 11/2003 | Braun et al. | |
| 6,718,199 B2 | 4/2004 | Thornton | |

(Continued)

OTHER PUBLICATIONS

"Methods for Manual Pure-Tone Threshold Audiometry", *American National Standard*, ANSI S3.21/2004 (ASA19-2004), Published by the American Institute for Physics for the Acoustical Society of America, pp. 1-13, (2004).

(Continued)

*Primary Examiner*—Max Hindenburg
*Assistant Examiner*—Jeffrey G Hoekstra
(74) *Attorney, Agent, or Firm*—Fredrikson & Byron, P.A.

(57) ABSTRACT

A method for developing and validating a quality assessment for a test is provided. A test method is also provided, which assesses the accuracy of a test. The methods include performing a behavioral test on a subject to measure a psychometric quantity, measuring one or more quality indicators, the quality indicators being any variables that are correlated with test accuracy, obtaining an independent measure of test accuracy, and deriving a predictive formula for estimating test accuracy from the quality indicators.

12 Claims, 12 Drawing Sheets

U.S. PATENT DOCUMENTS

| | | |
|---|---|---|
| 2003/0144603 A1 | 7/2003 | Zoth et al. |
| 2003/0232314 A1 | 12/2003 | Stout et al. |
| 2004/0116825 A1 | 6/2004 | Sturzebecher |
| 2004/0167380 A1 | 8/2004 | Simon |

OTHER PUBLICATIONS

Carhart, R., et al., "Preferred Method for Clinical Determination of Pure-Tone Thresholds", *Journal of Speech and Hearing Disorders*, 24 (4), pp. 330-345, (Nov. 1959).

Hughson, W., et al., "Manual for Program Outline for Rehabilitation of Aural Casualties Both Military and Civilian", *Supplement to the Transactions of the American Academy of Opthalmology and Otolaryngology*, pp. 3-15, (Jan. 1944).

Bekesy, G. Von, A New Audiometer, Acta Otolaryngol., 1947, pp. 411-422, vol. 34.

Byers, V.W., Two Methods of Measuring Recovery Following Short-Duration Fatigue, Journal of the Acoustical Society of America, May 1963, pp. 662-671, vol. 35, No. 5.

Campbell, R.A. and Lasky, E.Z., Adaptive Threshold Procedures: BUDTIF, Journal of the Acoustical Society of America, 1968, pp. 537-541, vol. 44, No. 2.

Carhart, R. and Jerger, J.F., Preferred Method for Clinical Determination of Pure-Tone Thresholds, Journal of Speech and Hearing Disorders, Nov. 1959, pp. 330-345, vol. 24, No. 4.

Cornsweet, T.N., The Staircase-Method in Psychophysics, American Journal of Psychology, 1962, pp. 485-491, vol. 75.

Green, D.M. and Swets, J.A., Signal Detection Theory and Psychophysics, 1974, pp. 265-271, Robert E. Krieger Publishing Co., Huntington, N.Y.

Harris, J.D., Proem to a Quantum Leap in Audiometric Data Collection and Management, Journal of Auditory Research, 1978, pp. 1-29, vol. 18, Supplement 7.

Humer, Larry E., Psychoacoustic Foundations of Clinical Audiology, Katz, J. (Ed.), Handbook of Clinical Audiology, 1985, pp. 94-115, Third Edition, Williams & Wilkins, Baltimore, MD.

Jerger, J., Bekesy Audiometry in Analysis of Auditory Disorders, Journal of Speech and Hearing Research, Sep. 1960, pp. 275-287, vol. 3, No. 3.

Jerger, J. and Herer, G., Unexpected Dividend in Bekesy Audiometry, Journal of Speech and Hearing Disorders, Nov. 1961, pp. 390-396, vol. 26, No. 4.

Jokinen, K., Presbyacusis. I. Comparison of Manual and Automatic Thresholds, Acta Otolaryngol., 1969, pp. 327-335, vol. 68(4).

Laroche, C. and Hetu, R., A Study of the Reliability of Automatic Audiometry by the Frequency Scanning Method (Audioscan), Audiology, 1997, pp. 1-18, vol. 36, No. 1.

Levitt, H., Transformed Up-Down Methods in Psycho-Acoustics, The Journal of the Acoustical Society of America, 1971, pp. 467-477, vol. 49.

Lutman, M.E., Cane, M.A. and Smith, P.A., Comparison of Manual and Computer-Controlled Self-Recorded Audiometric Methods for Serial Monitoring of Hearing, British Journal of Audiology, 1989, pp. 305-315, vol. 23.

Margolis, R.H. and Small, Jr., A.M., Masking with Narrow-Band FM Noise, The Journal of the Acoustical Society of America, Aug. 1974, pp. 692-694, vol. 56.

Marshall, L. Hanna, T.E. and Wilson, R.H., The Effect of Step Size on Clinical and Adaptive 2IFC Procedures in Quiet and in a Noise Background, Journal of Speech and Hearing Research, Aug. 1996, pp. 687-696, vol. 39.

Marshall, L. and Jesteadt, W., Comparison of Pure-Tone Audibility Thresholds Obtained with Audiological and Two-Interval Forced-Choice Procedures, Journal of Speech and Hearing Research, 1986, pp. 82-91, vol. 29.

Musiek, F.E. and Rintelmann, W.F. (Eds.), Contemporary Perspectives in Hearing Assessment, 1999, pp. 3-20, Allyn and Bacon, Boston, MA.

Roeser, R.J. and Clark, J.L., Clinical Masking, in Roeser, R.J., Valente, M. and Hosford-Dunn, H. (Eds.), Audiology Diagnosis, 2000, pp. 253-279 (Chapter 12), Thieme Medical Publishers, New York.

Roeser, R.J., Valente, M. and Hosford-Dunn, H., (Eds.), Audiology Diagnosis, 2000, Thieme Medical Publishers, New York.

Rudmose, W., Automatic Audiometry, Modern Developments in Audiology, edited by J. Jerger, 1963, pp. 30-75, Academic Press, New York.

Sakabe, N., Hirai, Y. and Itami, E., Modification and Application of the Computerized Automatic Audiometer, Scand. Audiol., 1978, pp. 105-109, vol. 7.

Schlauch, R.S. and Rose, R.M., Two- Three-, and Four-Interval Forced-Choice Staircase Procedures: Estimator Bias and Efficiency, The Journal of the Acoustical Society of America, Aug. 1990, pp. 732-740, vol. 88.

Sieminski, L., Automatic Audiometry, Otolaryngol. Clin. North Am., Oct. 1978, pp. 701-708, vol. 11(3).

Taylor, M.M. and Creelmann, C.D., PEST: Efficient Estimates on Probability Functions, The Journal of the Acoustical Society of America, 1967, pp. 782-787, vol. 41, No. 4.

Zwislocki, J.J. and Relkin, E.M., On a Psychophysical Transformed-Rule Up and Down Method Converging on a 75% Level of Correct Responses, Proceedings of the National Academy of Sciences, 2001, pp. 4811-4814, vol. 98.

\* cited by examiner

PREDICED AMTAS/MANUAL DIFFERENCES

METHOD FOR ASSESSING THE ACCURACY OF TEST RESULTS

FIELD OF THE INVENTION

The invention provides a method for developing a quality assessment method for quantitatively assessing the accuracy of test results. The invention also provides a test system and method which quantitatively assesses the accuracy of test results. In particular, the invention provides a system and method which qualitatively assesses the accuracy of the results of a hearing test.

BACKGROUND OF THE INVENTION

Many tests are provided which measure a behavior, e.g., a response or reaction to some kind of stimuli. For example, with hearing tests, a person is often asked to respond by pressing a button when he or she hears a sound. Other behavioral tests of this type include but are not limited to 1) tests of sensory sensitivity to physical stimuli including tests of hearing, vision, tactile sensation, and olfaction; 2) tests of cognitive function; 3) aptitude tests; 4) academic achievement tests and 5) personality tests. A typical prior art test method is illustrated in FIG. 1. An examiner administers a test to measure a psychometric quantity (step 1'). The psychometric quantity is usually measured by tracking a behavioral response or reaction to some kind of stimuli or question (step 2'). The results of these behavioral tests are typically displayed in some tangible form (step 3'). For example, the results of a hearing test are often displayed in the form of an audiogram. Sometimes, the results are further converted into a percentile rank, grade, category or the like. Prior art methods do not measure any other variables or behaviors seen during the test other than the response which determines the psychometric quantity measurement. Prior art methods also do not have any mechanism for quantitatively assessing the accuracy of test results.

It is often difficult from looking at the display of a given test result alone to determine whether the results are accurate. The accuracy of a given test result can vary due to a number of factors. For example, accuracy can be decreased when the test is taken by an unreliable subject. An unreliable subject may not always be truthful in answering test questions or may not respond to a stimulus or respond when there is no stimulus. Likewise, a subject with previous test taking experience may not be as reliable, as the subject may have too much knowledge of the test methods, such as tricks or elements of surprise used with the test. It would be desirable to be able to tell from the face of a test result whether the subject was reliable or not.

The accuracy of a test can also vary depending on the particular test procedure or methodologies used by a test examiner. Some procedures may produce more accurate results than others or an examiner may take shortcuts in administering the test, which decreases the accuracy. Even if an examiner was required to follow a strictly standardized method, it is difficult to tell from the face of a test result whether the standard method was properly followed. Thus, it is desirable to provide for more automated and standardized testing methods to ensure that the same method is always used.

The experience of the examiner may also affect the test accuracy, as more experienced examiners tend to produce more accurate test results. In the case of hearing tests, these tests are generally performed manually and audiologists often vary in their methods of performing the hearing test. Also, an experienced audiologist often subjectively evaluates the quality of an audiogram also taking into consideration observances seen during the test, but which do not show up on an audiogram, e.g., an observance of one or more false positive responses. However, an inexperienced audiologist may not make these observances and would only objectively evaluate the hearing test based on the audiogram only. It would be desirable to provide a test method wherein the test results are not affected by the experience of the examiner.

Further, if an examiner reviews a test result of a test given by another examiner, he or she does not have any indication as to the accuracy of the test and will not be able to take any subjective factors into consideration since he or she did not perform the test. Likewise, the examiner who actually performed the test may later review the results but not remember the subjective factors taken into consideration. This greatly limits the ability to compare test results across examiners. Often times, the only way to remedy this problem is to perform another test, which requires the use of more personnel and resources. Thus, it would be desirable to qualitatively assess a test result and to provide one or more quality indicators to allow an objective person to assess the quality and accuracy of the test given.

SUMMARY OF THE INVENTION

A method for developing a quality assessment for a test is provided. The method includes performing a behavioral test on a subject to measure a psychometric quantity, measuring the psychometric quantity to provide a test measurement of the psychometric quantity, measuring one or more quality indicators to provide one or more quality indicator measurements, the quality indicator being any variable that gives an indication of test accuracy, obtaining an independent measurement of the psychometric quantity for the subject, calculating a difference between the test measurement and the independent measurement, determining a relationship between the quality indicator measurements and the difference between the test measurement and the independent measurement, and using the relationship to predict a difference between the test result and the independent measure of the psychometric quantity, the difference being a quantitative measure of test accuracy.

The step of performing a behavioral test can be accomplished by providing stimuli to the subject and receiving, from the subject, responses to the stimuli. Also, the step of measuring one or more quality indicators can be accomplished by measuring quality indicators based upon variables seen when the stimuli is provided or when the responses are received. The quality indicators can be a behavior, e.g., a subject behavior. The step of obtaining an independent measurement includes performing a method for measuring the psychometric quantity that is regarded as an accurate method for measuring that psychometric quantity. In some cases, the step of obtaining an independent measurement includes performing a standardized test method for measuring the psychometric quantity.

Further, the step of determining a relationship between the quality indicator measurements and the difference between the test measurement and the independent measurement can include performing a multiple regression or other statistical measure for the quality indicator measurements and the difference between the test measurement and the independent measurement. The step of using the relationship to predict a difference between the test result and the independent measure of the psychometric quantity comprises deriving a predictive formula based on the relationship, the predictive formula being used to calculate an estimated test accuracy from the quality indicators. In some cases, the predictive formula is derived from a multiple regression performed for the quality indicator measurements and the difference between the test measurement and the independent measurement. In preferred cases, the predictive formula is $QA=Q_t-Q_m=f(QI_n)$.

A test method is also provided in some embodiments. The test method includes performing a behavioral test on a subject to measure a psychometric quantity, measuring the psychometric quantity to provide a test measurement of the psychometric quantity, measuring one or more quality indicators to provide one or more quality indicator measurements, the quality indicator being any variable that gives an indication of test accuracy, and calculating an estimated test accuracy using the one or more quality indicator measurements. The step of performing a behavioral test can include providing stimuli to the subject and receiving, from the subject, responses to the stimuli. Further, the step of measuring one or more quality indicators comprises measuring quality indicators based upon variables seen when the stimuli is provided or when the responses are received.

Also, the step of calculating an estimated test accuracy can include inputting the one or more quality indicator measurements into a predictive formula, the predictive formula being derived from a multiple regression performed for quality indicator measurements and a difference between a test measurement and an independent measurement obtained for a previously tested subject. The step of calculating an estimated test accuracy can also include inputting the one or more quality indicator measurements into a predictive formula, the predictive formula being derived by a method including performing a behavioral test on a subject to measure a psychometric quantity, measuring the psychometric quantity to provide a test measurement of the psychometric quantity, measuring one or more quality indicators to provide one or more quality indicator measurements, the quality indicator being any variable that gives an indication of test accuracy, obtaining an independent measurement of the psychometric quantity for the subject, calculating a difference between the test measurement and the independent measurement, determining a relationship between the quality indicator measurements and the difference between the test measurement and the independent measurement, and deriving a predictive formula based on the relationship, the predictive formula being used to calculate an estimated test accuracy from the quality indicator measurements.

In this step of calculating an estimated test accuracy, the step of determining a relationship between the quality indicator measurements and the difference between the test measurement and the independent measurement can be accomplished by performing a multiple regression for the quality indicator measurements and the difference between the test measurement and the independent measurement. In this case, a predictive formula is derived from the multiple regression.

The test method can further include a step of comparing the estimated test accuracy to other estimated test accuracy measurements obtained for a population group. This can be accomplished by presenting the estimated test accuracy as a percentile rank that compares with the other estimated test accuracy measurements. The population group preferably comprises one or more subjects having one or more characteristics in common. The test method can also include a step of comparing each quality indicator measurement to corresponding quality indicator measurements obtained for a population group. This can also be accomplished by presenting each quality indicator measurement as a percentile rank that compares with the corresponding quality indicator measurements.

A hearing test method is also provided in some embodiments, which includes performing a hearing test on a subject to measure the subject's hearing, measuring at least one quality indicator to provide a quality indicator measurement, the quality indicator being any variable that gives an indication of reliability of the hearing test, and calculating an estimated test accuracy using the one or more quality indicator measurements. The hearing test is preferably an automated test. In some embodiments, the quality indicators measured in the hearing test are selected from the group consisting of masker alert rate, time per trial, average number of trials for a threshold, total elapsed time, false alarm rate, average test-retest difference, quality check fail rate, air-bone gap >50 dB and air-bone gap <−10 dB.

The step of performing a hearing test to measure a subject's hearing can include providing, to the subject, a sequence of acoustic stimuli, receiving, from the subject, responses from the sequence of acoustic stimuli, and identifying hearing threshold levels based on the subject's responses. In some cases, the acoustic stimuli of the sequence can be adaptively selected based upon the subject's responses. Also, the step of measuring at least one quality indicator can be accomplished by measuring at least one quality indicator based upon a variable seen when the acoustic stimuli is provided and the responses are received.

In some embodiments, the step of performing a hearing test to measure a subject's hearing can be accomplished by presenting air-conducted acoustic stimuli to the subject, collecting responses from the subject, the responses being based on the air-conducted acoustic stimuli, identifying threshold levels based on the subject's responses to the air-conducted acoustic stimuli, presenting bone-conducted acoustic stimuli to the subject, collecting responses from the subject, the responses being based on the bone-conducted acoustic stimuli, and identifying threshold levels based on the subject's responses to the bone-conducted acoustic stimuli. When the hearing test is accomplished in this way, the step of measuring at least one quality indicator can include measuring at least one quality indicator based upon a variable seen during presentation of and responses to the air-conducted and bone-conducted acoustic stimuli.

In other embodiments, the step of performing a hearing test to measure a subject's hearing can be accomplished by presenting a plurality of tone frequencies to the subject, identifying a first ear and a second ear of the subject based on a threshold level of a tone frequency, the first ear having a lower threshold at the first tone frequency, and the second ear having a higher threshold at the first tone frequency, performing air-conduction tests on the subject's first ear and then second ear, and performing bone-conduction tests on each ear.

In some cases, the step of calculating an estimated test accuracy includes inputting the one or more quality indicator measurements into a predictive formula, the predictive formula being derived from a multiple regression performed for quality indicator measurements and a difference between a test measurement and an independent measurement obtained for a previously tested subject. In other cases, the step of calculating an estimated test accuracy includes inputting the one or more quality indicator measurements into a predictive formula, the predictive formula being derived by a method including performing a hearing test on a subject to measure hearing threshold levels, measuring the threshold levels to provide a test measurement, measuring one or more quality indicators to provide one or more quality indicator measurements, the quality indicator being any variable that gives an indication of test accuracy, obtaining an independent measurement of the hearing threshold levels for the subject, calculating a difference between the test measurement and the independent measurement, determining a relationship between the quality indicator measurements and the difference between the test measurement and the independent measurement, and deriving a predictive formula based on the relationship, the predictive formula being used to calculate an estimated test accuracy from the quality indicator measurements. The step of determining a relationship between the quality indicator measurements and the difference between the test measurement and the independent measurement, in some cases, includes performing a multiple regression for the quality indicator measurements and the difference between the test measurement and the independent measurement.

The hearing test method can further include comparing the estimated test accuracy to other estimated test accuracy measurements obtained for a population group. This can be accomplished by presenting the estimated test accuracy as a percentile rank that compares with the other estimated test accuracy measurements. The population group preferably includes one or more subjects having one or more characteristics in common. In some cases, the characteristic is a hearing characteristic. The hearing test method can even further include comparing each quality indicator measurement to corresponding quality indicator measurements obtained for a population group. This can also be accomplished by presenting each quality indicator measurement as a percentile rank that compares with the corresponding quality indicator measurements.

A method for testing hearing of a subject is also provided in some embodiments. The method includes performing an automated hearing test and tracking quality indicators during the hearing test, wherein the quality indicators include a masker alert rate, time per trial, average number of trials for a threshold, total elapsed time, false alarm rate, average test-retest difference, quality check fail rate, air-bone gap >50 dB and air-bone gap <−10 dB.

DETAILED DESCRIPTION OF THE PREFERRED EMBODIMENTS

In some embodiments, the invention provides test methods for quantitatively assessing the accuracy of test results. The methods include identifying one or more quality indicators which give an indication of test reliability and then measuring those quality indicators during the test. These quality indicators allow an objective person to assess the accuracy of the test and/or test result. The use of these quality indicators allow for more tests to be automated, since examiners are not needed on-site to subjectively evaluate the accuracy of the test. In turn, skilled examiners will have more time to devote their expertise to those who need it most, such as infants, young children, seniors and/or developmentally delayed individuals and/or persons who are too ill for automated testing.

Figure 2:
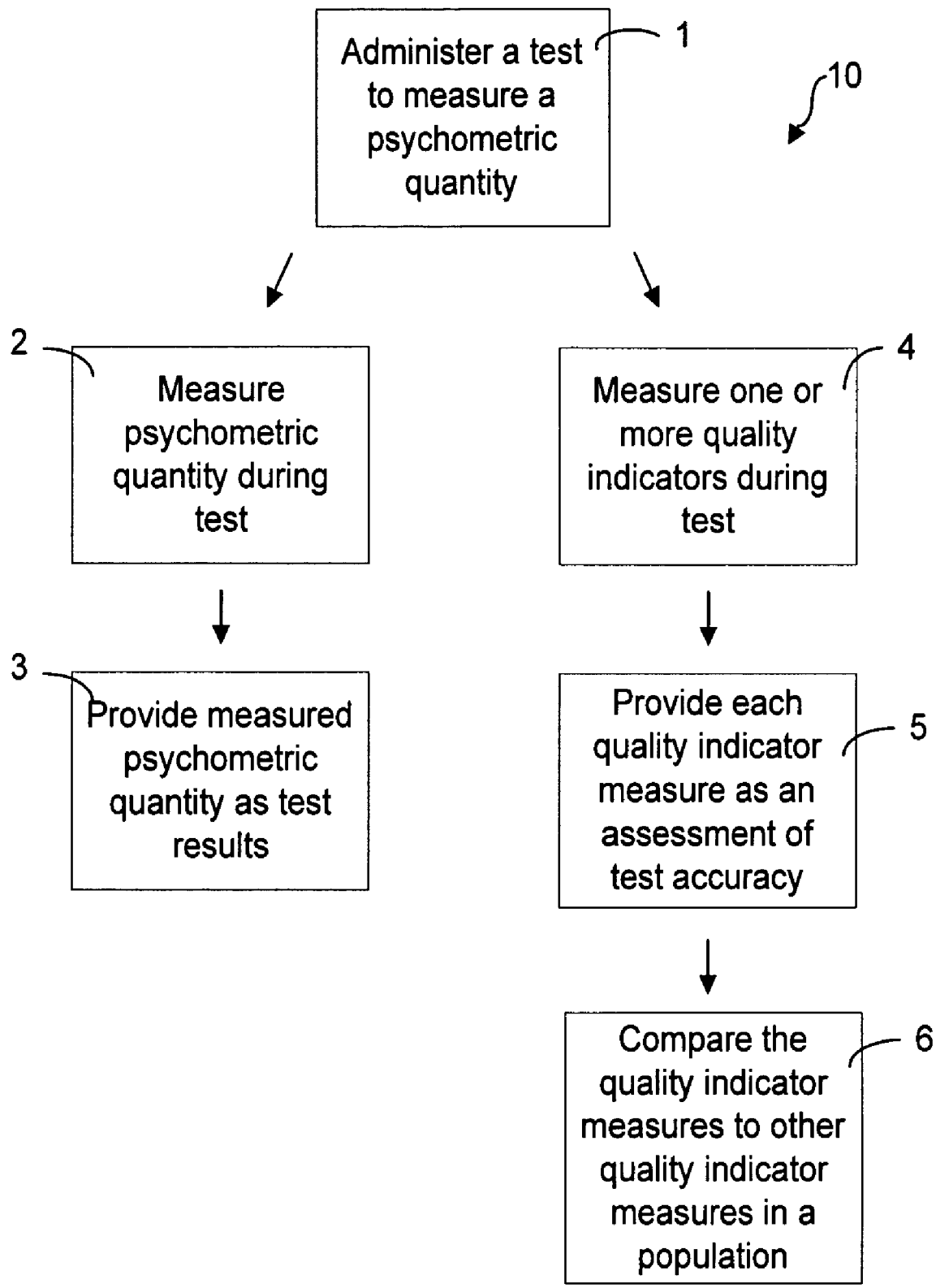
FIG. 2 is a flow diagram of the steps of a method according to an embodiment of the invention.

FIG. 2 diagrams the steps of a behavioral test method 10 according to an embodiment of the invention. An examiner administers a test on a subject to measure a psychometric quantity (step 1). The psychometric quantity is generally the main focus of the test. The test to measure the quantity is any behavioral test which generally requires an examiner to measure one or more behavioral responses to stimuli, such that the aggregate of the responses provide a quantitative measure of the psychometric quantity. The stimuli can be physical signals, images or questions which require behavioral responses. Any behavioral test is within the scope of the invention and include but are not limited to 1) tests of sensory sensitivity to physical stimuli including tests of hearing, vision, tactile sensation, and olfaction; 2) tests of cognitive function; 3) aptitude tests; 4) academic achievement tests and 5) personality tests. The test can be administered on the subject manually or automatically. In preferred embodiments, the test is administered automatically. For example, the test can be carried out by a software program.

While administering the test, the examiner measures the psychometric quantity (step 2). In the case of sensory tests, an examiner keeps track of the subject's responses to physical stimuli. For example, an examiner presents a stimulus and allows the subject to indicate whether he or she sensed that stimulus. The examiner tracks the subject's responses and then later provides the test results in some tangible form (step 3). The test results are generally a measure of the psychometric quantity. Also, while measuring the psychometric quantity (step 2), the examiner also measures one or more quality indicators (step 4). Quality indicators are any measurable variables or behaviors which may be related to the quality of the subject's responses to the set of stimuli. The quality indicators correlate with test accuracy such that the measurements of the quality indicators indicate whether or not the test results are accurate. The quality indicator could also be one which shows whether or not the examiner administered the test in a standard and reliable form. The quality indicators are then provided to help an independent person determine whether the test and the results are accurate (step 5). At the end of the test, a test diagnostic can be provided which includes both the test results and quality indicators.

Figure 3:
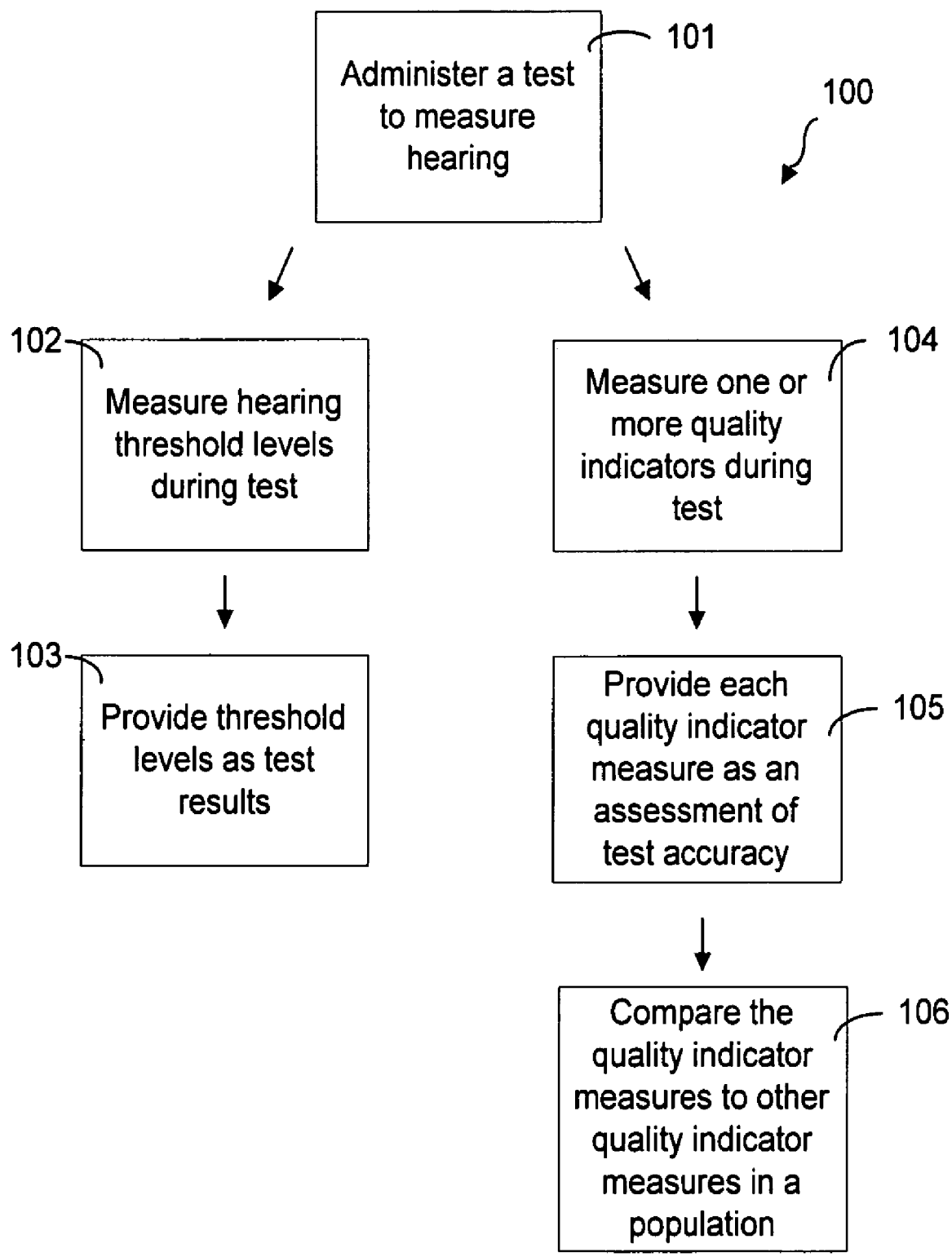
FIG. 3 is a flow diagram of the steps of a hearing test method according to an embodiment of the invention.

FIG. 3 depicts a hearing test method 100 according to another embodiment of the invention the hearing test method also employing the use of quality indicators to assess test accuracy. An examiner administers a test to measure a subject's hearing (step 101). Any hearing test is within the scope of the invention. The hearing test can also be automated or performed manually. In preferred cases, the test is an automated test, which is driven by a computer, audiometer, software program or the like. During the test, the subject's hearing threshold levels at various sound frequencies are identified (step 102). A threshold level is the lowest intensity of a stimulus at a given frequency that a subject can hear. The threshold levels are provided as the results of the hearing test (step 103). At the same time the subject's threshold levels are being identified, the examiner or computer driven program tracks or measures one or more quality indicators (step 104). The quality indicators are those which correlate to test accuracy for a specific test. The quality indicators used may differ depending on the specific test method used. At the end of the test, an audiogram can be provided which includes both the hearing threshold levels and the quality indicators.

Figure 4:
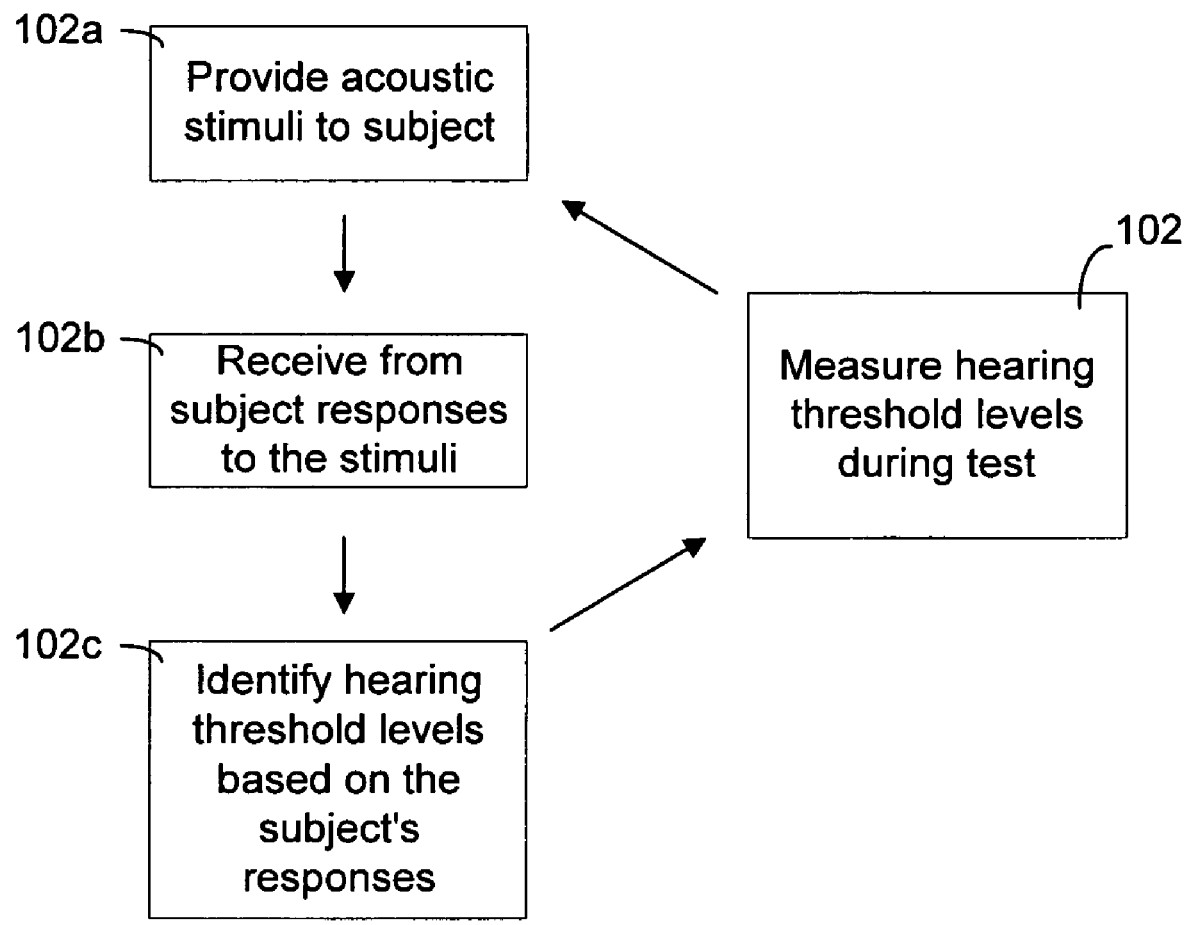
FIG. 4 is a flow diagram of the steps of a portion of a hearing method shown in FIG. 3 according to an embodiment of the invention.

The hearing test can be any test known in the art and the step of measuring threshold levels (step 102) can be accomplished according to any procedure known in the art. Preferably, the hearing test is one that conforms to the National Standard Methods for Manual Pure-Tone Audiometry (ANSI S3.21-1978) or automated methods that employ the principles embodied in that standard. Referring to FIG. 4, in many cases, this step (step 102) is accomplished by providing a set of acoustic stimuli to the subject and asking the subject to respond when he or she hears a stimulus (step 102a). Each stimulus is typically a puretone stimulus and can be an air-conducted stimulus or a bone-conducted stimulus. The stimuli are presented to the subject at different frequencies and intensities. The examiner or computer-driven program receives from the subject responses to the stimuli (step 102b). Based on the responses received, the subject's threshold levels at various sound frequencies are identified (step 102c). A standard clinical pure-tone audiogram is comprised of thresholds for tonal stimuli varying in frequency between 250 and 8000 Hz presented by air-conduction and by bone-conduction.

Figure 5:
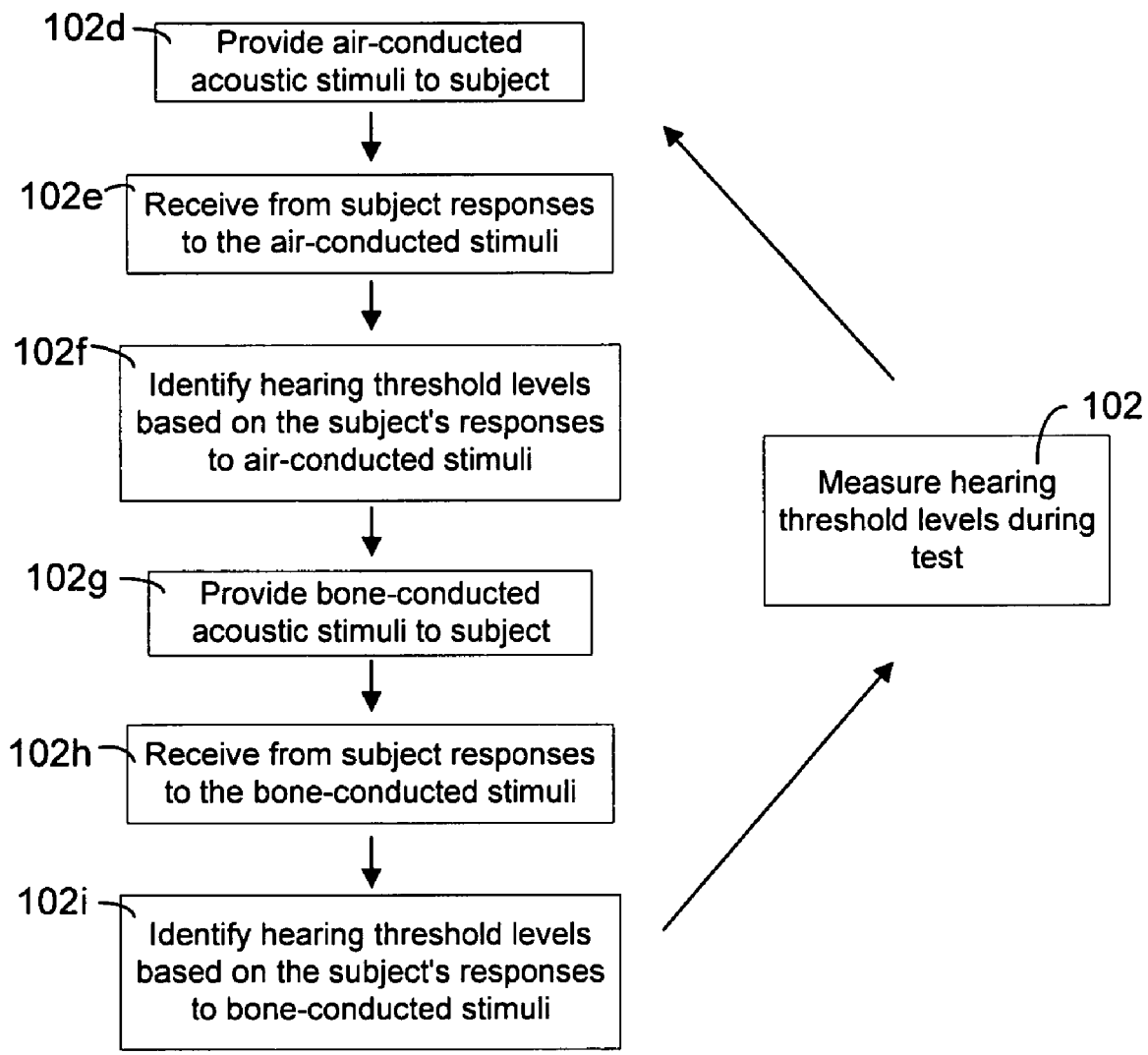
FIG. 5 is a flow diagram of the steps of a portion of a hearing method shown in FIG. 3 according to another embodiment of the invention.

The hearing test can also include more than one different part, procedures or types of testing. For example, referring to FIG. 5, the step of measuring threshold levels (step 102) includes both air-conduction and bone-conduction testing. First, air-conduction stimuli are presented to the subject (step 102d). Air-conduction transducers are placed over or in the subject's ears and then stimuli are delivered through the transducers to each ear. The subject's responses to the air-conduction stimuli are received and collected (step 102e) and then based on those responses, the subject's air-conduction hearing threshold levels are identified (step 102f). Then, the air-conduction transducers are replaced with a bone-conduction transducer and bone-conduction stimuli are provided through the transducer to the subject (step 102g). Sometimes air-conducted masking noise is presented to the non-test ear during testing to insure that the non-test ear is not hearing the stimuli. The subject's responses to the bone-conduction stimuli are received and collected (step 102h) and then based on those responses, the subject's bone-conduction hearing threshold levels are identified (step 102i). Both the air-conduction and bone-conduction thresholds are later provided on the audiogram. Again, while any different procedures and types of hearing tests can be used, the quality indicators used may also differ depending on the procedures used. The quality indicators used are any which correlate to test accuracy for the given test. Thus, in some embodiments, methods of testing are provided wherein one or more variables other than a psychometric quantity being measured are also measured and provided in the form of quality indicators to allow one to assess the accuracy of the test given.

In particular embodiments, a method for developing a quality assessment method is provided. This method includes identifying one or more quality indicators that can be measured using a given test and then evaluating those quality indicators to determine whether they correlate with test accuracy. The quality indicators are generally evaluated as a combination using any method known in the art to determine whether they correlate with test accuracy for a particular test. This method is performed to determine whether a given set of quality indicators can be used with a given test.

Figure 6:
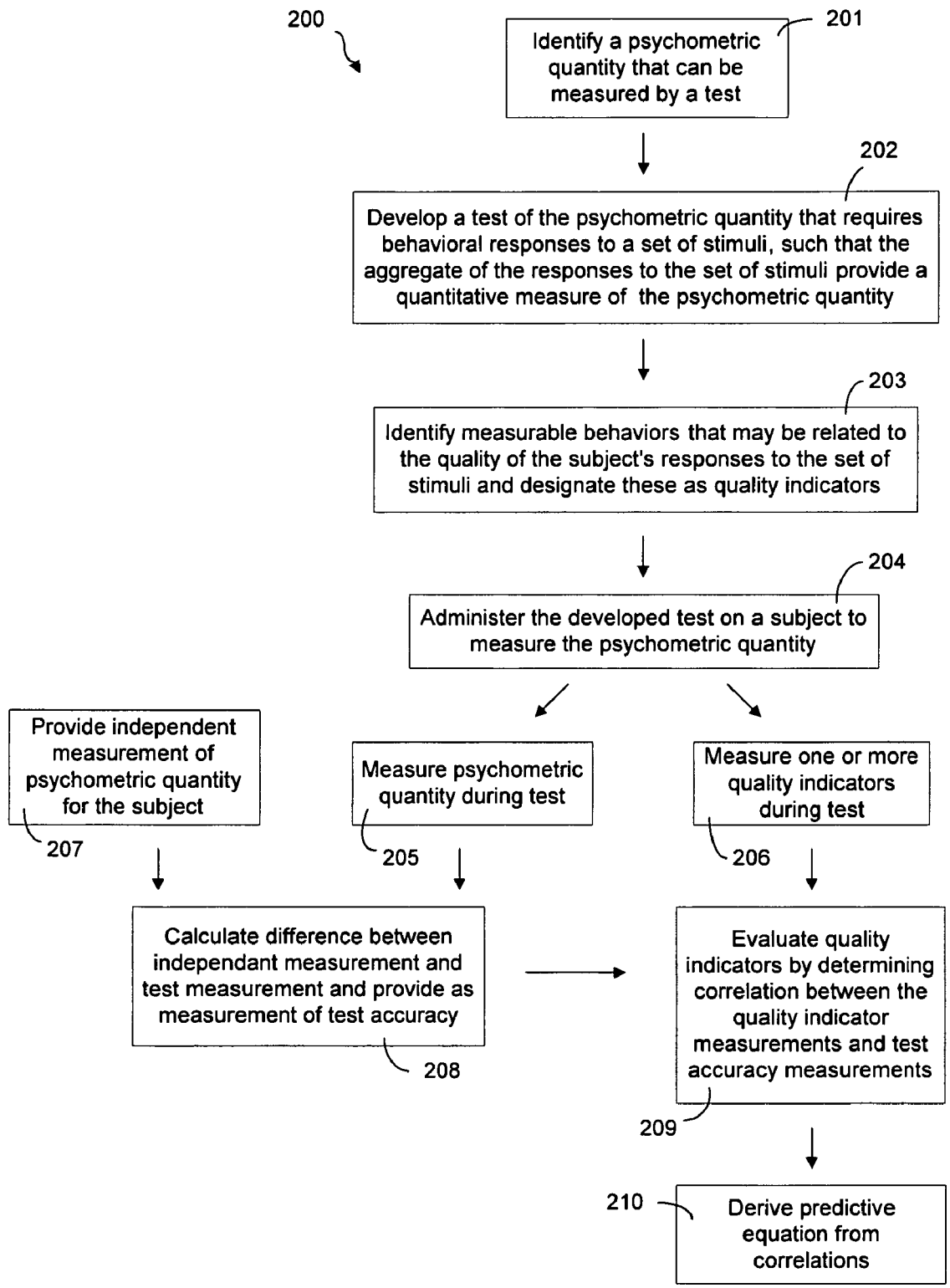
FIG. 6 is a flow diagram of the steps of method of developing a quality assessment method according to an embodiment of the invention.
Figure 7:
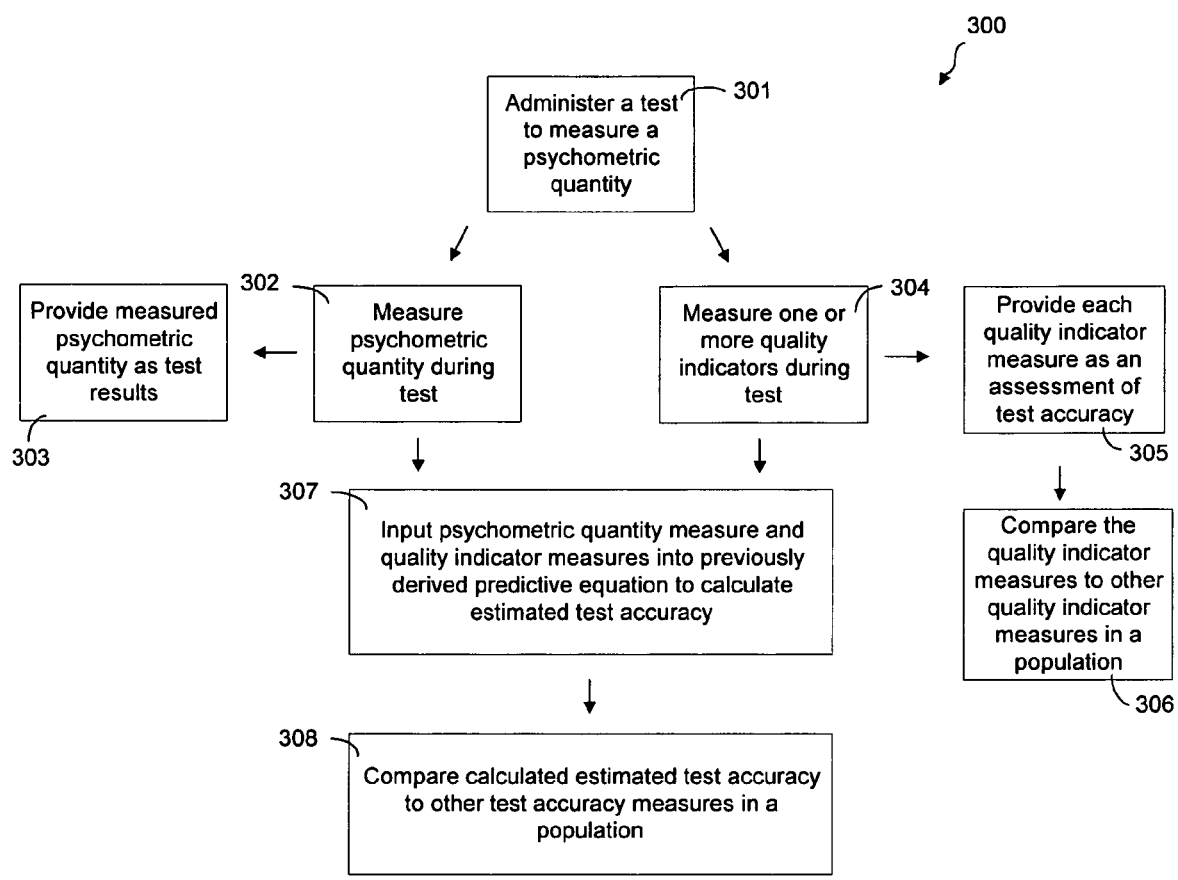
FIG. 7 is a flow diagram of the steps of a quality assessment method according to an embodiment of the invention.

FIG. 6 illustrates a method 200 for developing a quality assessment method according to a particular embodiment. An examiner identifies a psychometric quantity that can be measured by a given test (step 201). Next, the examiner develops a test for measuring that psychometric quantity (step 202). Of course, the examiner may also select a known test for measuring a psychometric quantity and use this instead of developing a new test. The test may require behavioral responses to a set of stimuli, such that the aggregate of the responses to the set of stimuli provide a quantitative measure of that psychometric quantity. The examiner also identifies one or more measurable behaviors or variables (i.e., quality indicators) that can be detected and measured during the test (step 203). Methods of detecting and measuring these quality indicators may also be developed, and these methods will be used during the test.

Once the test has been developed, the examiner then administers the test (step 204). During the test, the psychometric quantity is measured (step 205) and also the quality indicators are measured (step 206). Also, an independent measurement of the psychometric quantity is also separately obtained and then provided (step 207). The independent measurement is separately obtained for the same subject and may be one that is regarded as an accurate measurement by those who are experts in the art. For example, the independent measurement can be obtained using a standardized test method on the subject for measuring the psychometric quantity.

The examiner next calculates the difference between the test results obtained with the test and the independently provided measurement (step 208). This calculation is provided as a measurement of test accuracy. Next, the examiner determines any correlation between the variable measurements and the measurement of test accuracy (step 209). For example, the correlation can be determined by placing the quality indicator measurements into a multiple regression with the measurement for test accuracy. This multiple regression returns a regression coefficient, which is the correlation between the measurement of test accuracy and all of the quality indicators combined. The higher the correlation is, the better the quality indicators are. If a good correlation between the quality indicators and test accuracy is obtained, those quality indicators can then be used with that test method to determine the accuracy of the test result. If a poor correlation is obtained, the development method is repeated using different quality indicators or those quality indicators which do not contribute to the strength of the regression are discarded. This development method can be repeated until a good correlation is obtained (and therefore good quality indicators of that method are developed).

Once a good correlation between test accuracy and quality indicators are obtained, the examiner derives a predictive formula that can be used to calculate an estimated test accuracy from the quality indicators. In some cases, the predictive formula can be derived from the correlations between the quality indicators and the measure of test accuracy. For example, in cases where a multiple regression is used to determine the correlation between the quality indicators and test accuracy, the multiple regression also produces a formula for calculating an estimated test accuracy from the quality indicators. In some cases, the predictive formula may take the form $QA=Q_i-Q_m=f(QI_n)$. In using this formula, a psychometric quantity Q is measured by the test. The test of Q requires behavioral responses to a set of stimuli $S_n$, such that the aggregate of the responses to $S_n$ provide a quantitative measure $Q_m$ of Q. During the test of Q, n measurable behaviors $QI_n$ are also measured that may be related to the quality of the subjects' responses to $S_n$. An independent measure of Q, $Q_i$, is provided, against which $Q_m$ can be compared. This predictive formula can then be used to calculate estimated test accuracy on future subjects.

In some embodiments, the examiner can further a develop a mechanism for characterizing or categorizing the estimated test accuracy or QA. For example, in some embodiments, the examiner performs the developed test on several subjects in a population group and obtains an estimated test accuracy or QA for the population group. The Examiner then compares the obtained QA for a subject to the QAs obtained for the population group. The QA can be presented as a percentile rank that compares with the measurements of the population group or QA can be categorized as "good", "fair" and "poor". In other cases, each measurement of QA for a population group is plotted against the estimated QA calculated by the formula on a graph (predicted versus measured QA graph). The measurements plotted on the graph can then divided into areas of poor, fair and good. Once a QA is obtained for a subject, it can then be categorized as poor, fair or good depending on where QA falls within the graph.

Each quality indicator measurement can be presented as a raw measurement. However, in some embodiments, the examiner can also a develop a mechanism for characterizing or categorizing the quality indicator measurements, either individually or in combination. For example, in some embodiments, the examiner performs the developed test on several subjects in a population group and obtains quality indicator measurements for the population group. The examiner can then compare each quality indicator measurement to the measurement obtained for that quality indicator for the population group. For example, the quality indicator measurement can be presented as a percentile rank that compares with the measurements of the population group or the quality indicator can be categorized as "good", "fair" and "poor". In other cases, the examiner compares the subject's combined quality indicator measurements to the combined quality indicator measurements for the population group.

In some cases, the population group wherein measurements of test accuracy are taken has at least one trait in common. For example, the population group can be a specific age group (for example, infants, children, adults and seniors), gender group and the like. In cases where the test given is a hearing test, the population group may have at least one hearing trait in common. For example, the population group can be a group having a pre-determined level of hearing (for example, normal hearing and hearing impaired). The hearing impaired group can be further broken down into groups with different types of a hearing loss (for example, normal hearing and hearing impaired). The hearing impaired group can be further broken down into groups with different types of hearing loss (for example, conduction hearing loss or sensorineural hearing loss) or into groups with different degrees of hearing loss (for example, mild, severe and profound). An exemplary group would be "normal hearing male adults" or "mild conductive hearing loss male children".

Figure 8:
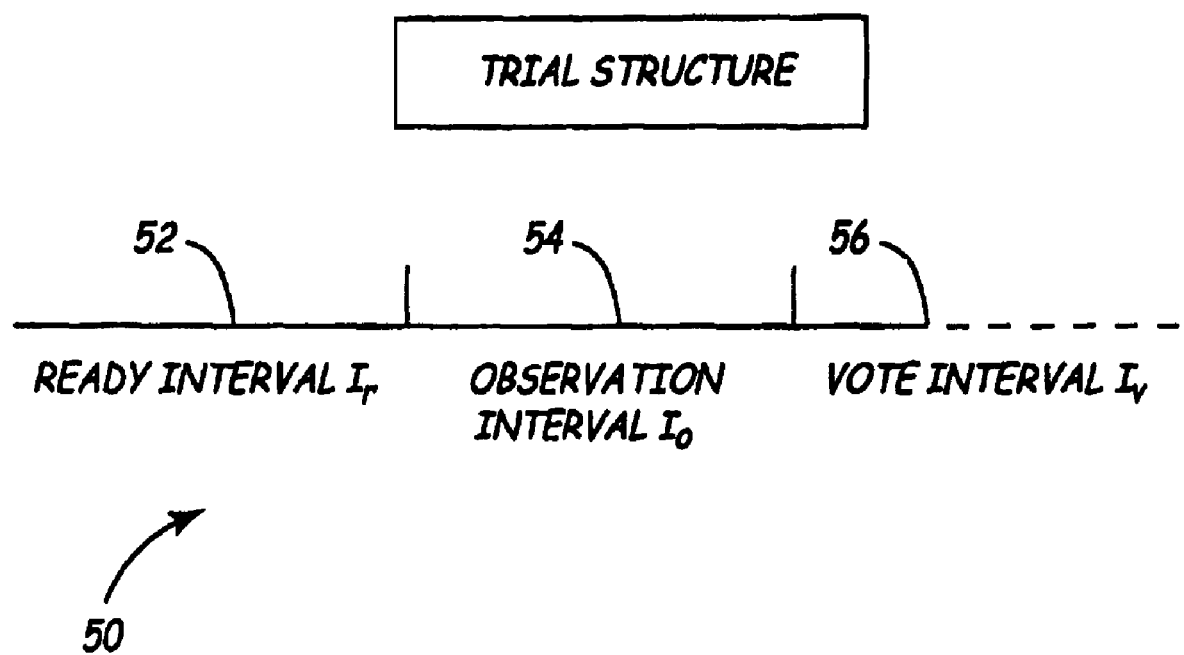
FIG. 8 is a diagram of a trial of a hearing test according to an embodiment of the invention.
Figure 9:
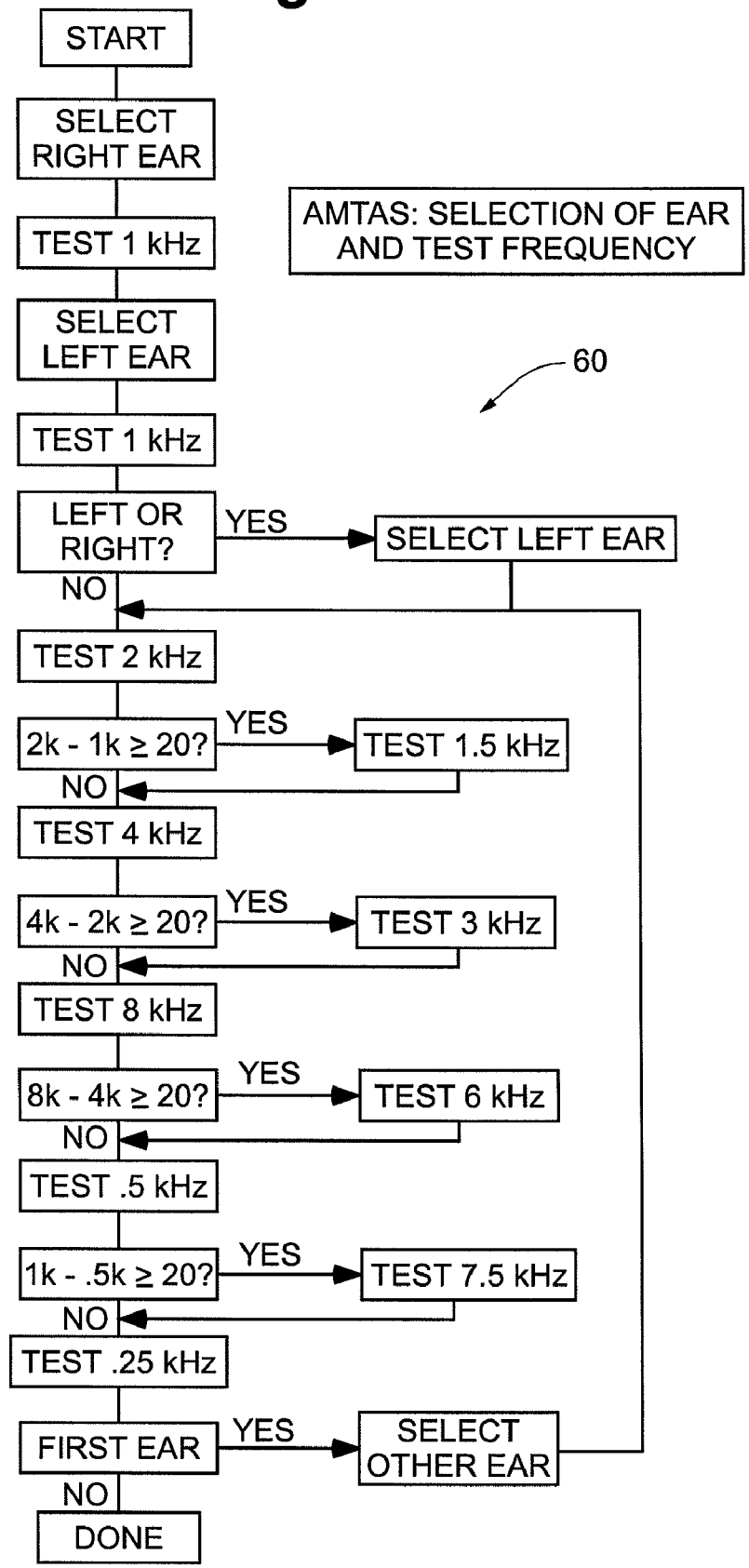
FIG. 9 is a flow diagram of the steps of a portion of a hearing test according to an embodiment of the invention, showing a method of selecting ear and test frequency.

Once a quality assessment method is developed, that method can be performed on test subjects. Test methods which assess the quality of test results are also provided in some embodiments of the invention. FIG. 8 illustrates a test method 300 according to a particular embodiment of the invention. An examiner administers a test to measure a psychometric quantity (step 301). The test in this embodiment is a behavioral test which requires the examiner to measure one or more behavioral responses to stimuli, such that the aggregate of the responses provide a quantitative measure of the psychometric quantity. While administering the test, the examiner measures the psychometric quantity (step 302). The examiner tracks the subject's responses and then provides the tests results in some tangible form (step 303). While measuring the psychometric quantity (step 302), the examiner also measures one or more selected quality indicators (step 304). The quality indicators selected have already been evaluated and have been determined to correlate with test accuracy. Once the quality indicators are measured, they are provided as an assessment of test accuracy (step 305). For example, the quality indicators can be provided as absolute measurements. In some cases, the quality indicator measures are also compared against quality indicator measures obtained for a population group (step 306). For example, the quality indicators can be compared to the population group by expressing them as a percentile rank.

The psychometric quantity measure and quality indicator measures are also input into a predictive formula for calculating estimated test accuracy (step 307). This predictive formula has previously been derived using a multiple regression analysis (as explained in the method of developing a quality assessment method) or some other method that produces a formula of the form $QA=Q_i-Q_m=f(QI_n)$. The calculated test accuracy is provided as a quantitative assessment of the accuracy of the results. The calculated estimated test accuracy can also be compared to measured test accuracies for the population group (step 308). For example, the calculated test accuracy can be expressed as a percentile rank comparing to those measured test accuracies in the population group.

The invention will now be described in accordance with a particularly preferred embodiment. A method of testing hearing automatically is provided. The method both measures auditory detection thresholds for a variety of sound stimuli and also detects a variety of quality indicators. The specific method of testing hearing used in this embodiment is the AMTAS™ test, a test described in U.S. Pat. No. 6,496,585, the entire contents of which are incorporated herein by reference. AMTAS is a software driven system which automatically carries out the method on the subject, as described in U.S. Pat. No. 6,496,585. The AMTAS method is an adaptive method. Acoustic stimuli are first delivered to the subject and the subject responds to the stimuli. The stimuli are delivered at different frequencies and at different levels for each frequency. If the subject detects a stimulus, he or she will respond in a "Yes" fashion and if the subject does not, he or she will respond in a "No" fashion. The method adaptively selects the frequency and level of the next stimulus to be delivered based on the subject's previous responses. The method determines threshold levels for each frequency tested. The AMTAS procedure will now be described in more detail, with reference to Table 1, which contains a definition of terms.

TABLE 1

| Term | Definition |
|---|---|
| Trial | A sequence of temporal intervals corresponding to one stimulus presentation |
| Ready Interval | The first temporal interval of a trial; the interval preceding the stimulus |
| Observation Interval | The temporal interval following the ready interval; the interval in which the stimulus is presented |

TABLE 1-continued

| Term | Definition |
| --- | --- |
| Vote Interval | The temporal interval following the observation interval; this interval begins at the offset of the observation interval and ends when the subject responds |
| Level | The level of a stimulus; for auditory stimuli the level may be a specified sound pressure level or hearing level |
| Initial Level (40 dB HL) | The level of the first stimulus presentation in a threshold determination |
| Initial Increment (10 dB) | The amount that the level is incremented when a "No" response occurs to the initial level |
| Stimulus Decrement (10 dB) | The amount that the level is decremented when a "Yes" response occurs |
| Stimulus Increment (5 dB) | The amount that the level is incremented following "No" responses that occur after the first "Yes" response |
| Maximum Level | Maximum value of a level for a specified stimulus |
| Criterion Level | The level corresponding to a "Yes" response immediately preceded by a "No" response. |
| Threshold Criterion | Number of times the criterion level must occur at a given level to meet the definition of a threshold level |
| Threshold Level | Level corresponding to threshold; level at which the criterion level occurs at the threshold criterion |
| Number of Stimuli | Number of stimulus presentations required to determine a threshold level |
| Masking Criterion | In the masking mode, the minimum level for which masking is presented to the non-test ear |
| Interaural Attenuation | The estimated difference in stimulus level in the test ear and non-test ear |
| Masker Level | The level of the masking noise presented to the non-test ear |
| Masker Level at Threshold | The level of the masking noise presented to the non-test ear when the test signal level is a threshold level |
| Test-Retest Difference at 1 kHz or 0.5 kHz | Difference threshold level for two 1 kHz or 0.5 kHz threshold measures |
| Catch Trial | A trial for which the observation interval contains no stimulus |
| Catch Trial Probability (20%) | The probability that a trial will be a catch trial |
| False Response Probability | Proportion of "Yes" responses in catch trial; determined for each test stimulus |
| Feedback | Information provided to subject indicating that a "Yes" vote occurred during a catch trial |
| Octave Threshold Difference Criterion | Difference between adjacent octave frequencies above which the interoctave frequencies above which the interoctave frequency is tested |

During the AMTAS hearing test, threshold levels for certain sound frequencies are determined for each of a set of air and bone conducted stimuli. The examiner selects which frequencies to test or the software program can select a default set of frequencies to test. The frequencies are preferably selected from the table listed below.

TABLE 2

Test Frequencies (kHz)

| Air | 0.125 | 0.25 | 0.5 | 0.75 | *1.0* | 1.5 | *2.0* | 3.0 | *4.0* | 6.0 | 8.0 |
| Bone | — | 0.25 | 0.5 | 0.75 | *1.0* | 1.5 | *2.0* | 3.0 | *4.0* | — | — |

*Default Frequencies are shown in italics.

The default set of frequencies include those frequencies that are required for a diagnostic hearing evaluation. When the default set is used, additional frequencies are automatically tested when needed. The AMTAS method includes a sequence of trials, wherein a stimulus is presented in each trial. A trial is a sequence of temporal intervals corresponding to a single stimulus presentation. Several trials are presented having a stimulus at a given frequency, wherein in many of those trials, the frequency is presented at a different level.

FIG. 8 illustrates a typical trial structure. Each frequency is tested by presenting to the subject a stimulus at a given frequency at different levels. The program determines which level of each frequency the subject can barely hear, and that level is determined to be a threshold level. Each trial 50 consists of a ready interval 52, an observation interval 54 followed by a vote interval 56. The stimulus is presented during the observation interval 54. The subject responds during the vote interval 56 by pushing a Yes button if a stimulus was detected or by pushing a No button if no stimulus was detected during the observation interval. The vote interval 56 has a variable duration, as it begins when the observation interval ends and ends when the subject responds. Trials are presented repetitively at various stimulus levels at a given frequency until the threshold level is determined for that frequency. The process is repeated for all examiner specified stimuli or for the default set of stimuli.

Catch trials are presented randomly to determine the subject's reliability. Catch trials are trials in which no stimulus is presented. Feedback is used to inform the subject that he are she falsely responded Yes during a catch trial. For example, a false alarm light or message can be provided, which indicates when the subject has responded Yes during a catch trial.

AMTAS testing begins with air-conduction testing for each ear and then proceeds with bone-conduction testing. The air-conduction testing is completed first. FIG. 8 illustrates a flowchart 60 of an AMTAS process for air-conduction testing according to a preferred embodiment. The flowchart 60 illustrates the logic for the selection of test frequency and test ear for air-conduction testing using the default stimulus set. The default initial test ear for air-conduction testing is the right ear. For air-conduction testing, the default order of test frequencies is the following: 1 kHz, 2 kHz, 4 kHz, 8 kHz, 0.5 kHz, and 0.25 kHz. Interoctave frequencies (0.75 kHz, 1.5 kHz, 3 kHz, and 6 kHz) are automatically tested when the difference between two adjacent octave frequencies exceeds D, where D is a predetermined value. The default value of D is 20 decibels (dB).

The test begins by determining the threshold level at 1 kHz for the right ear and then for the left ear. The test ear which is subsequently tested is the ear with the better threshold level at 1 kHz. The better ear is tested at the next selected frequency. For example, with the default set of frequencies, the better ear would then be tested at 2 kHz. Then, that ear would be tested at the next frequency. This process continues until threshold levels are determined for all of the selected frequencies for that ear. At the end of the test for the better ear, the test is repeated at 1 kHz unless the threshold level is more than the maximum level, where the maximum level is the maximum value of a level for a specified stimulus, in which case 0.5 kHz is retested. Then, the same process is used to test the other ear.

After air-conduction testing is completed, the examiner is prompted to place the bone-conduction transducer behind the ear with the poorer threshold level at 1 kHz (or 0.5 kHz). An earphone is placed over the non-test ear for masking. If the default bone-conduction stimulus set is selected, the frequencies are tested in the following order: 1 kHz, 2 kHz, 4 kHz, 0.5 kHz, and 0.25 kHz. After all frequencies are tested, the examiner is prompted to reverse the transducer and the other ear is tested. Alternatively, the bone conduction transducer can be placed on the forehead and earphones can be placed on both ears for masking.

When the test signal may be audible in the non-test ear, a masking signal is presented to ensure that perception of the test signal by the non-test ear does not affect the test. When testing with air-conducted stimuli, masking is presented to the non-test ear in the observation interval when the level is greater than the masking criterion. The masking criterion is the level at which the stimulus may be audible in the non-test ear of a normal hearing subject for a given stimulus/transducer combination. The masking level presented to the contralateral ear is the level minus the average intraaural attenuation plus 10 dB. The masking level and intraaural attenuation values are dependent on the stimulus and the transducer. The masking level and intraaural attenuation values in Table 3 may be used for two commonly used audiometric transducers. When testing with bone-conducted stimuli, the non-test ear is always masked.

TABLE 3

Interaural Attenuation and Masking Criteria

| Transducer | Frequency (kHz) | 0.125 | 0.25 | 0.5 | 0.75 | 1.0 | 1.5 | 2.0 | 3.0 | 4.0 | 6.0 | 8.0 |
|---|---|---|---|---|---|---|---|---|---|---|---|---|
| TDH-50 | Average Interaural Attenuation at 5 dB | 40 | 40 | 40 | 40 | 40 | 40 | 45 | 45 | 50 | 50 | 50 |
|  | Masking Criterion | 30 | 30 | 30 | 30 | 30 | 30 | 35 | 35 | 40 | 40 | 40 |
| ER-3A | Average Interaural Attenuation at 10 dB | 75 | 75 | 75 | 75 | 70 | 55 | 50 | 50 | 50 | 50 | 50 |
|  | Masking Criterion | 65 | 65 | 65 | 65 | 60 | 45 | 40 | 40 | 40 | 40 | 40 |
| Bone Conduction | Average Interaural Attenuation |  | 0 | 0 | 0 | 0 | 0 | 0 | 0 | 0 |  |  |
|  | Masking Criterion |  | 0 | 0 | 0 | 0 | 0 | 0 | 0 | 0 |  |  |

Figure 10:
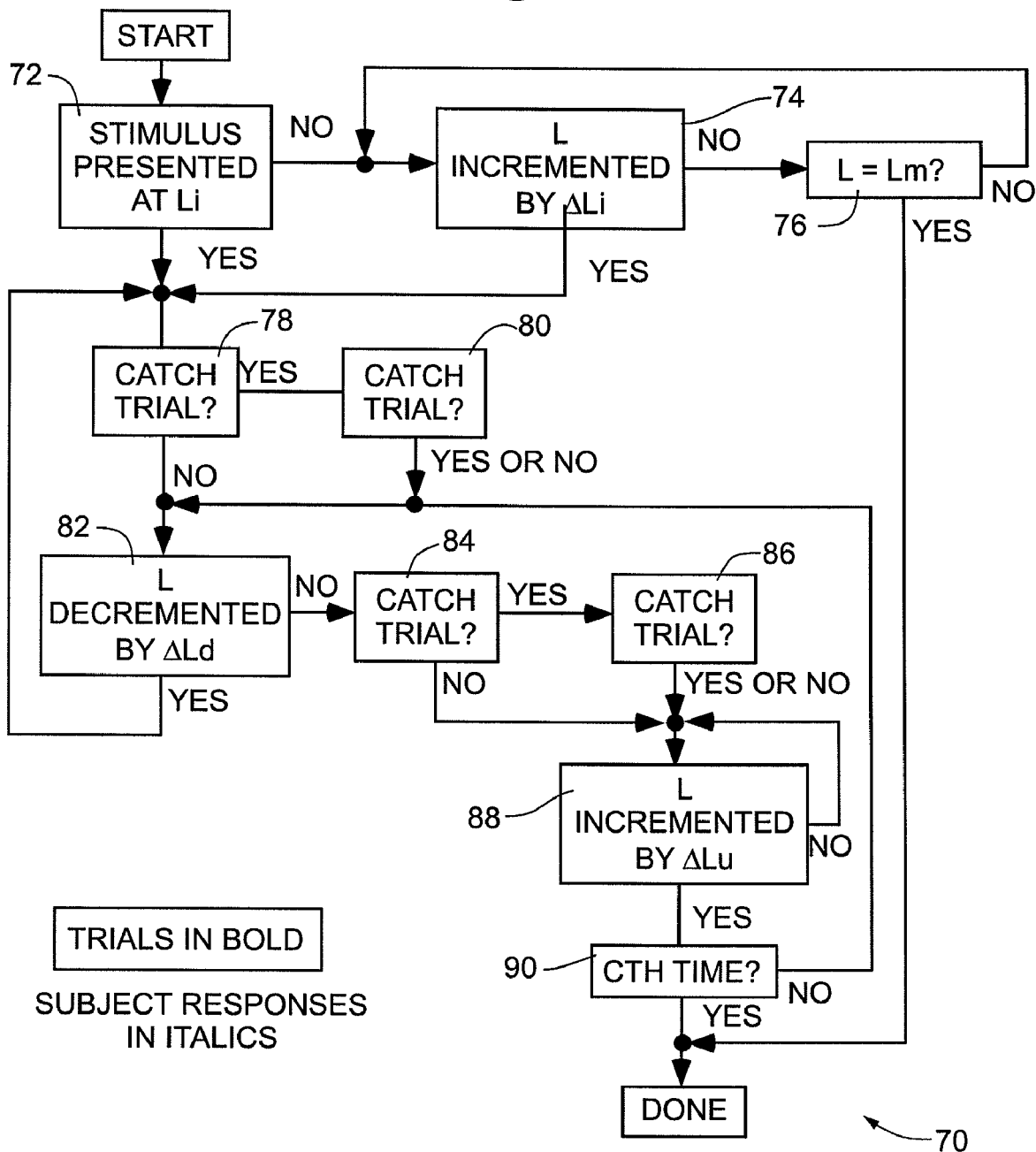
FIG. 10 is a flow diagram of the steps of a portion of a hearing test according to an embodiment of the invention, showing a method of determining threshold levels for a given test frequency.

FIG. 10 illustrates an adaptive method 70 for determining a threshold level of a given frequency by adaptively varying the level of a stimulus. The threshold level is the lowest level at which the subject hears a tone at least 50% of the time. The adaptive method 70 includes initial step 72, increment step 74, maximum threshold step 76, catch trials 78 and 80, decrement step 82, catch trials 84 and 86, increment step 88, and C value step 90. This method can be used for testing each of the selected frequencies.

In operation, the initial stimulus is presented at an initial level (40 dB) to the subject at the initial step 72. If the subject responds "No" to the initial stimulus, the level of the next stimulus is presented at the initial level of 40 dB plus 10 dB (50 dB total) at the increment step 74. The increment step 74 is repeated by incrementing the level by 10 dB until a "Yes" response occurs or until the level reaches the maximum level. If the level reaches the maximum level, then the threshold level is greater than the maximum level. In this case, the subject is considered to not be able to detect any levels for that frequency.

If the subject responds "Yes" to the initial stimulus at the initial level of 40 dB, a catch trial 78 is performed to provide an indication of the subject's reliability. If the subject responds "Yes" to the catch trial 78, then a false alarm light 44 illuminates and another catch trial 80 is performed. Regardless of the subject's response to catch trial 80, testing continues. If, however, the subject responds "No" to the catch trial 78, testing continues without performing the catch trial 80.

When testing continues, the level of the next stimulus is presented at the previous level minus 10 db at the decrement step 82. After each "Yes" response, catch trials 78 and 80 are performed again, and the level is subsequently decremented by 10 dB. If the subject responds "No" at the decrement step 82, catch trials 84 and 86 are performed as described above for catch trials 78 and 80. For each "No" response after the first "Yes" response at decrement step 82, the level is incremented by 5 dB at the increment step 88.

The level that produces a "Yes" response immediately preceded by a "No" response is designated the criterion level. When the criterion level occurs C times at the same level, where C is the threshold criterion, that level is designated the threshold level. This is illustrated by C value step 90. The default value of C is 2, but the examiner can set C to be any value. The adaptive method 70 is repeated for each examiner-selected frequency or for the default frequency set.

After determination of air-conduction and bone-conduction thresholds, the program determines threshold measurements for which masking levels may not have been appropriate. The program alerts the examiner of these threshold measurements and these are known as masking alerts. The examiner may be prompted to retest those thresholds, and appropriate masker levels may be automatically selected. Examples of suitable masking alerts which can be used are given in Table 4.

TABLE 4

Masking Alerts

| Air Conduction | Masker level is ≦ air conduction threshold level of non-tested ear |
|  | Masker level is ≦ bone conduction threshold level of non-tested ear |
| Bone Conduction | Masker level is ≦ air conduction threshold level of non-tested ear |
|  | Masker level - Interaural Attenuation is ≦ bone conduction threshold level of non-tested ear |

While the AMTAS method tests a subject's hearing, the method also tracks the quality indicator variables shown in Table 5 and produces a measure of each at the conclusion of the test. The measure of each quality indicator is also displayed on or along with the audiogram. Each of these quality indicators are described in further detail below.

TABLE 5

| QUALITY INDICATORS | DEFINITION |
|---|---|
| Masker Alert Rate | The number of thresholds for which the masking noise presented to the non-test ear may have been either too low or too high divided by the number of measured thresholds. |
| Time per Trial | The average elapsed time for all observation intervals |
| Average No. Trials for Threshold | The total number of observation intervals divided by the number of measured thresholds |
| Elapsed Time | The total elapsed time for the test |
| False Alarm Rate | The number of false alarms (trials in which the subject reported the presence of a stimulus when no stimulus was presented) divided by the total number of catch trials (trials in which there was no stimulus) |
| Average Test-Retest Diff | The average difference in threshold measures obtained for stimuli that were tested twice |
| QC Fail Rate (%) | The total numbered of occurrences of quality check fails (failure to respond to stimuli presented above threshold) divided by the number of measured thresholds |
| Air-Bone Gap > 50 dB | Number of air-bone gaps (difference between thresholds obtained for air- and bone-conducted stimuli for each frequency/ear combination) that exceed 50 dB |
| Air Bone Gap < −10 dB | Number of air-bone gaps (difference between thresholds obtained for air- and bone-conducted stimuli for each frequency/ear combination) that are less than −10 dB |

Masker Alert Rate

During testing, air-conducted and bone-conducted acoustic stimuli are presented to each ear of a subject. Some subjects can hear better in one ear than the other ear. Sometimes, the stimuli presented to the non-test ear may still be high enough to be detected by the non-test ear, especially when the non-test ear is better than the test-ear. If a subject detects a stimulus in the non-test ear, he or she may still respond although the stimulus was not detected by the test ear. This false response decreases the accuracy of the hearing test.

The hearing test of the current embodiment seeks to remedy this by presenting a masking signal to the non-test ear to ensure that any detections of stimuli by the non-test ear do not affect the test. When testing with air-conducted stimuli, masking is presented to the non-test ear when the stimulus level is higher than a masking criterion. The masking criterion is the level at which the stimulus may be audible in the non-test ear of a normal hearing subject for a given stimulus/transducer combination. When testing with bone-conducted stimuli, the non-test ear is always masked. A masking signal typically sounds like a static sound and is often very different in sound from the acoustic stimuli presented to the test-ear, so the two sounds will not be confused.

While the use of a masking signal in the non-test ear improves the accuracy of the test, the masker level might be too high so that it is detected by the test-ear. If the masker level is too high, it may actually prevent the test ear from detecting the test signal. Of course, if the masker level is too low, then it fails to serve its masking purpose. Thus, a masking dilemma is sometimes seen, wherein there is no masker level that masks the test ear without being audible in the non-test ear, and this decreases test accuracy.

As a result of the masking dilemma, it is beneficial to alert an audiologist to the areas of the test wherein the dilemma may have occurred. The present method alerts audiologists by tracking a masker alert rate quality indicator. The masker alert rate is the number of thresholds for which the masking noise presented to the non-test ear may have been either too low or too high divided by the number of measured thresholds. When the alert rate is too high, this will alert the audiologist that the masker level may have been too high or too low during many of the threshold measurements. Thus, a high masker alert rate suggests that the test results are less than accurate.

Once the masker alert rate is determined, in some embodiments, the rate can then be compared against an independent or standard masker alert rate measurement. The standard masker alert rate measurement can be the average rate obtained for a specific group. Often times, the specific group will also have a characteristic in common, for example age or hearing ability.

Time Per Trial

The hearing test in this embodiment includes a sequence of trials, wherein a stimulus is presented in each trial. For each trial, a stimulus is presented in the observation interval and the subject responds during the vote interval. The subject may respond quickly during the vote interval or may take a longer time to respond. Thus, the elapsed time for the vote interval is dependant completely on the subject's response time. A subject who responds too quickly may be rushing through the test, which decreases the test accuracy. Similarly, a subject who takes too long to respond may not be understanding the test or may not be sure in his or her responses, which also decreases test accuracy.

In order to alert an audiologist to these potential concerns, a time per trial quality indicator is tracked during the test. The time per trial quality indicator is the average elapsed time for all trials in the test. If the elapsed time is too high or too low, the accuracy of the test may have been compromised. Once the time per trial is determined, in some embodiments, the time can then be compared against an independent or standard time per trial measurement.

Average Number of Trials for Threshold

In an adaptive procedure, the stimulus level is dependent on the response to the stimulus in the previous trial. Threshold is found according to a set of rules when the subject has responded above a certain level and failed to respond below a certain level, that level being the subjects threshold. The more consistent the subject, the fewer trials are required to obtain threshold. Thus, it is helpful to know the number of observation intervals that were needed in order to obtain a threshold.

The hearing test method of this embodiment tracks an average number of trials for threshold quality indicator to determine whether a larger than normal number of observation intervals were needed to obtain threshold measurements. This quality indicator is the total number of observation intervals divided by the number of measured thresholds in the test. If this number is too high, it suggests that too many observation intervals were needed to obtain threshold measurements, which decreases test accuracy. Once the average number of trials for threshold quality indicator is determined, in some embodiments, the number can then be compared against an independent or standard number.

Elapsed Time

The elapsed time for each trial, the reciprocal of the rate of stimulus presentation, is determined by the subject's response time, allowing the subject to control the pace of the test. For example, a subject that responds quickly during the vote interval of each trial will move through the test at a faster pace than a subject who does not respond quickly. Thus, the overall time needed to complete the test is variable. This permits the testing of subject's with a wide range of age, cognitive ability, reaction time and motor dexterity. If the total time needed to complete the test is too high or too low, this may suggest that the test is not as accurate. For example, a test completed in a very short amount of time may suggest that the subject was rushing through the test. The total elapsed time quality indicator can be, in some embodiments, compared against an independent time measurement. The independent measurement can be an average elapsed time for a given population group. There may be a different elapsed time for different subject groups. For example, the elapsed time for children may be larger than for adults, as children may need a longer amount of time to complete the test.

False Alarm Rate

Catch trials, trials in which no stimulus is presented, are performed at various points during the AMTAS method to determine the subject's reliability. If the subject responds "Yes" when no stimulus is presented, a false alarm occurs. False alarms are trials in which the subject reported the presence of a stimulus when no stimulus was presented. The false alarm rate is the number of false alarms divided by the total number of catch trials. If the subject often responds "Yes" when no stimulus is presented, the false alarm rate will be high, which indicates that the subject is less reliable. Once the false alarm rate is determined, the rate can then be compared against an independent rate measurement. The independent measurement can be an average rate for a given population group. There may be a different average false alarm rate used for different subject groups. For example, the average false alarm rate for adults may be lower than the average false alarm rate for children.

Average Test-Retest Difference

During air-conduction testing it is common to test one frequency, either 1 kHz or 0.5 kHz frequency twice (see FIG. 8) to obtain a measure of test-retest reliability. Air-conduction testing begins by determining the threshold level at 1 kHz for each ear, and then the thresholds for other frequencies are subsequently determined. At the end of air-conduction testing, once all of the selected frequencies are tested, the 1 kHz frequency may be tested again, unless the threshold level for the 1 kHz is more than the maximum level. If this is the case, the 0.5 kHz frequency is retested instead. The average test-retest difference quality indicator is a calculated. This quality indicator is the difference between the threshold level for the first 1 kHz (or 0.5 kHz) and the second 1 kHz (or 0.5 kHz). This difference measurement serves as a quality indicator because if the thresholds are different, he or she may not be reliable. If there is no difference, this shows the subject responded the same way for both tests and indicates that the subject is reliable. The higher the difference, the more likely that the subject is unreliable. Once this difference is determined, in some embodiments, this number can then be compared against an independent number.

Quality Check Fail Rate

Figure 1:
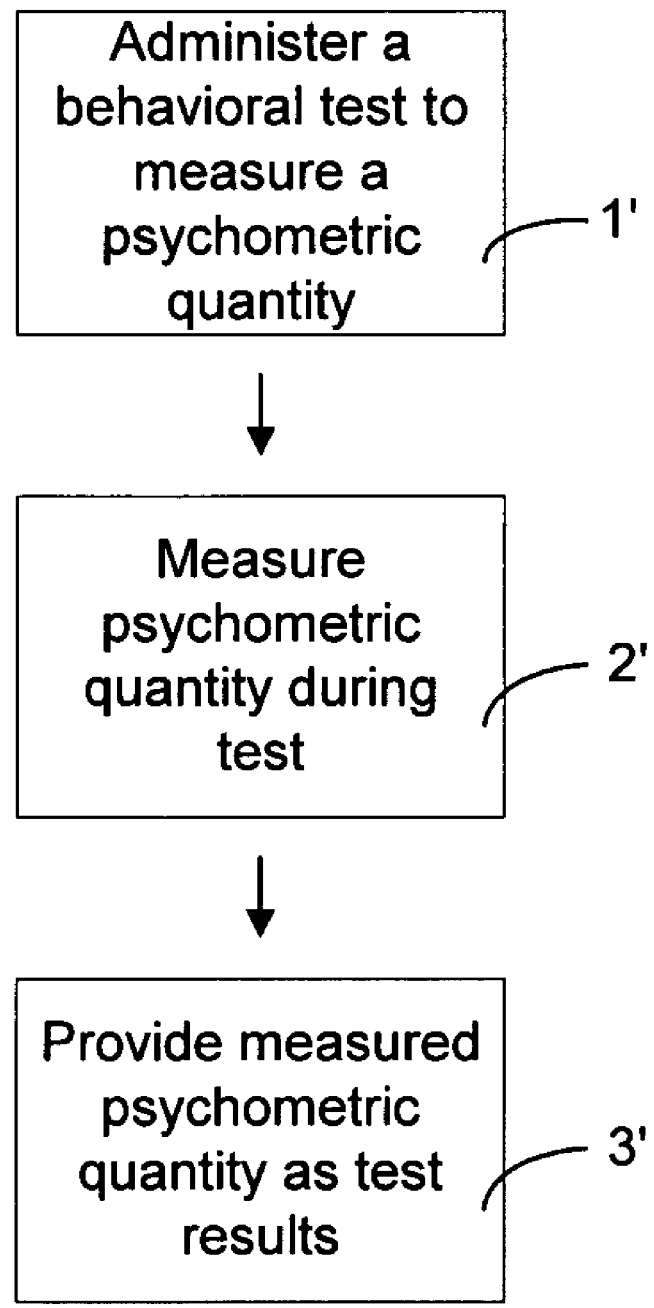
FIG. 1 is a flow diagram of the steps of a prior art method.

After a threshold is determined, e.g., by a method as illustrated in FIG. 1, a stimulus may be presented at a level 5 dB greater that the threshold level. A "No" response to this stimulus constitutes a quality check fail quality indicator. A quality check fail is an indicator that the measured threshold may be inaccurate. When a quality check fail occurs, threshold testing continues at the same frequency until a threshold is determined which is not followed by a quality check fail. The quality check fail rate is the number of quality check fails divided by the number of measured thresholds. Once this number is determined, in some embodiments, this number can then be compared against an independent number.

Air-Bone Gap >50 dB and <−10 dB

The AMTAS method determines the threshold level for a given frequency in a given ear through both air-conduction testing and bone-conduction testing. In some cases, the threshold level for a frequency and ear combination determined by air-conduction testing will be different than the level determined by bone-conduction testing. While some difference in threshold levels is to be expected (as the subject may have a hearing loss type which causes them to respond better to one type of testing than another), a threshold level difference of greater than 50 dB or less than −10 dB may indicate a problem with test accuracy. The air-bone gap >50 dB quality indicator is the number of air-bone gaps that exceed 50 db wherein the air-bone gap <−10 dB quality indicator is the number of air-bone gaps that are less than −10 db. The number of each of these air-bone gaps are tracked and presented at the end of the test. In some cases, each number can be compared to an independent air-bone gap number.

The quality indicators used in this particular method (illustrated in Table 5) have already been determined to correlate with test accuracy. For example, the AMTAS procedure was previously performed on a group of subjects to measure a psychometric quantity Q. In this case, Q is a set of threshold levels that were obtained during the AMTAS procedure. The measurement of Q, $Q_m$, was provided in the form of an audiogram. An independent measurement of Q, $Q_i$, was also provided for each subject. $Q_i$ was obtained by performing the same test manually by a well-trained, highly-experienced audiologist. For each threshold level, the estimated test accuracy, QA, was obtained by determining the absolute differences, $Q_i$-$Q_m$, in threshold levels obtained by AMTAS and by the manual method. The average absolute difference for all threshold levels employed in the test was QA.

At the same time QA was calculated, measurements for several quality indicators ($QI_n$) were also obtained. A predictive formula was also derived for these quality indicators by performing a multiple regression between the measurements for each quality indicator ($QI_n$) and the measurement of test accuracy (QA). Quality indicator measurements which did not contribute to the strength of the regression were discarded. Of the quality indicators listed in Table 5 average number of trials and elapsed time were discarded. For the remaining factors, the multiple regression returned a coefficient ($C_n$) and an intercept (K). The resulting formula is $$QA = Q_i - Q_m = f(QI_n) = \Sigma(C \cdot QI)_n + K$$

Note that QA relies only on $QI_n$ and not $Q_i$ or $Q_m$. This formula produces a calculation of the estimate of the accuracy of the test result (relative to results obtained by an expert professional). Its accuracy is determined by the strength of the multiple regression. This formula expresses the predicted difference between $Q_i$ and $Q_m$ and can be used prospectively for $Q_m$ data for which $Q_i$ is not available provided that the tested individual is a member of the population group used. This derived formula can be used on future subjects for calculating an estimate of the test accuracy based on the quality indicator measurements.

Furthermore, a mechanism for comparing a subject's QA to other QAs obtained for a population group was developed. In developing this mechanism, the AMTAS hearing test procedure was performed on 123 patients with varying degrees of hearing loss. During the AMTAS procedure, both the calculated test accuracy (QA) and also measurements for quality indicators were obtained. An independent hearing test was also manually performed on the same 123 patients. The independent hearing test was performed twice by two expert human testers. A data set, as shown in Table 6, was obtained for a group of subjects who were tested by two human testers and by AMTAS. A measurement of the average difference for two manual hearing tests was obtained. Table 6 shows summary data for seven quality indicators obtained on 123 patients with various degrees and types of hearing loss, as measured using the AMTAS procedure. Also shown are the average absolute differences between test results obtained with AMTAS and results from the manual method, which is a measure of test accuracy. The last column shows the predicted absolute difference between the results obtained with AMTAS and those obtained with the independent, manual method. The multiple correlation between the quality indicators and the measured test accuracy was 0.83, accounting for 69% of the variance.

TABLE 6

|  | Masker Alert Rate | Time per Rate | False Alarm Rate | Avg Test-Retest Diff | QC Fail Rate (%) | ABG >50 | BAG >10 | Avg Abs Diff | Pred Abs Diff |
|---|---|---|---|---|---|---|---|---|---|
| Mean | 0.1 | 3.8 | 0.1 | 5.0 | 2.2 | 0.7 | 0.7 | 8.6 | 1.0 |
| S.D. | 0.2 | 0.7 | 0.1 | 2.6 | 3.7 | 1.8 | 1.1 | 4.8 | 1.0 |
| Max | 1.1 | 6.5 | 0.4 | 12.5 | 17.9 | 9.0 | 7.0 | 31.8 | 5.5 |
| Min | 0.0 | 2.8 | 0.0 | 0.0 | 0.0 | 0.0 | 0.0 | 3.6 | 0.2 |
| 95th Percentile | 0.4 | 5.3 | 0.3 | 10.0 | 11.1 | 5.0 | 2.0 | 17.9 | 2.9 |

A mechanism for reducing QA to a categorical variable such as "good", "fair", and "poor" was also developed, using the data obtained for the population group of 123 patients. Categories may be based on the variance associated with QA or the variance associated with another data set that is thought to represent the desired distribution of QA. In this case, it was desirable for $Q_m$ to have the same statistical properties as a set of measures of the differences in results obtained by two expert human testers. The mean and variance associated with the data set shown in Table 6 were used to categorize QA by determining the distance (in standard deviation units) between each individual QA and the mean difference for two human testers. That is, if the mean absolute difference in thresholds obtained by two expert human testers is D and the standard deviation of D is SD, then the distance ($D_{QA}$) of QA from D is given by $$D_{QA}=(QA-D)/SD_D$$

$D_{QA}$ was converted to categorical data as shown in Table 7.

TABLE 7

| Difference | Category |
|---|---|
| $D_{QA} \leq 1$ | Good |
| $1 < D_{QA} \leq 2$ | Fair |
| $D_{QA} > 2$ | Poor |

Any useful number of categories may be derived in this manner, recognizing that as the number of categories increases, the number of errors in assigning a given value of $D_{QA}$ to a category increases as well. This process resulted in the occurrences of Good, Fair, and Poor results in the data set of the 123 individuals, as shown in Table 8.

TABLE 8

| Category | No. of Occurrences | % |
|---|---|---|
| Good | 91 | 74 |
| Fair | 20 | 16 |
| Poor | 12 | 10 |

Figure 11:
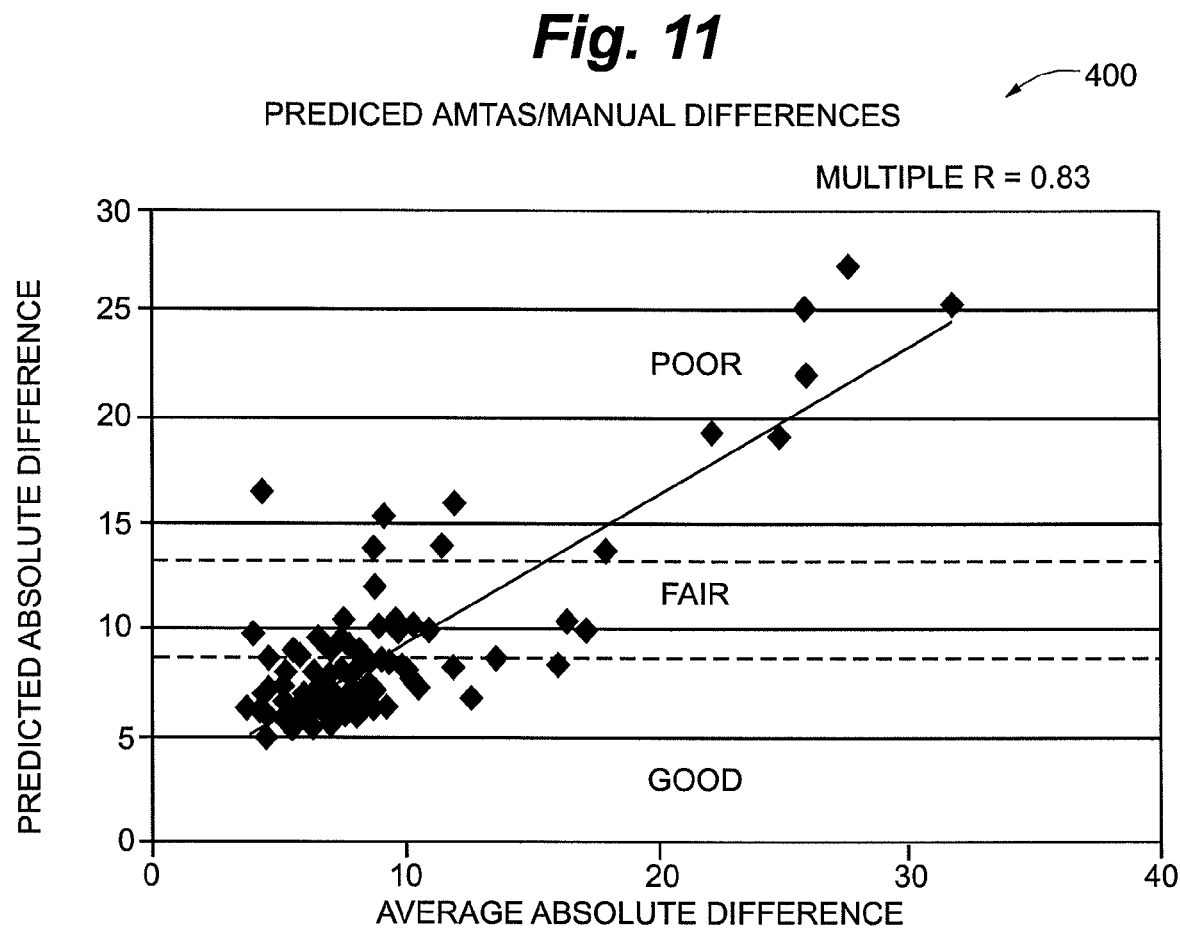
FIG. 11 is a graph illustrating estimated test accuracies and average test accuracies calculated for a population group.

The QA measures for the population group were also plotted on a graph, as shown in FIG. 11. The graph was also divided into areas of "good", "fair" or "poor" using the formula illustrated in Table 7, depending on where the other QA measures fall. Once a QA is obtained for any given subject, it can be placed into a category of "good", "fair" or "poor" depending on where that QA falls on the graph of FIG. 11.

A mechanism for comparing a subject's quality indicator measurements to measurements obtained for a population group was also developed. In this case, quality indicator measures were obtained for a population group and averaged, as shown in Table 6. These average measures can then be used to compare against a future subject's quality indicator measures. For example, the subject's quality indicator measures can be compared to the population group by expressing them as a percentile rank.

Figure 12:
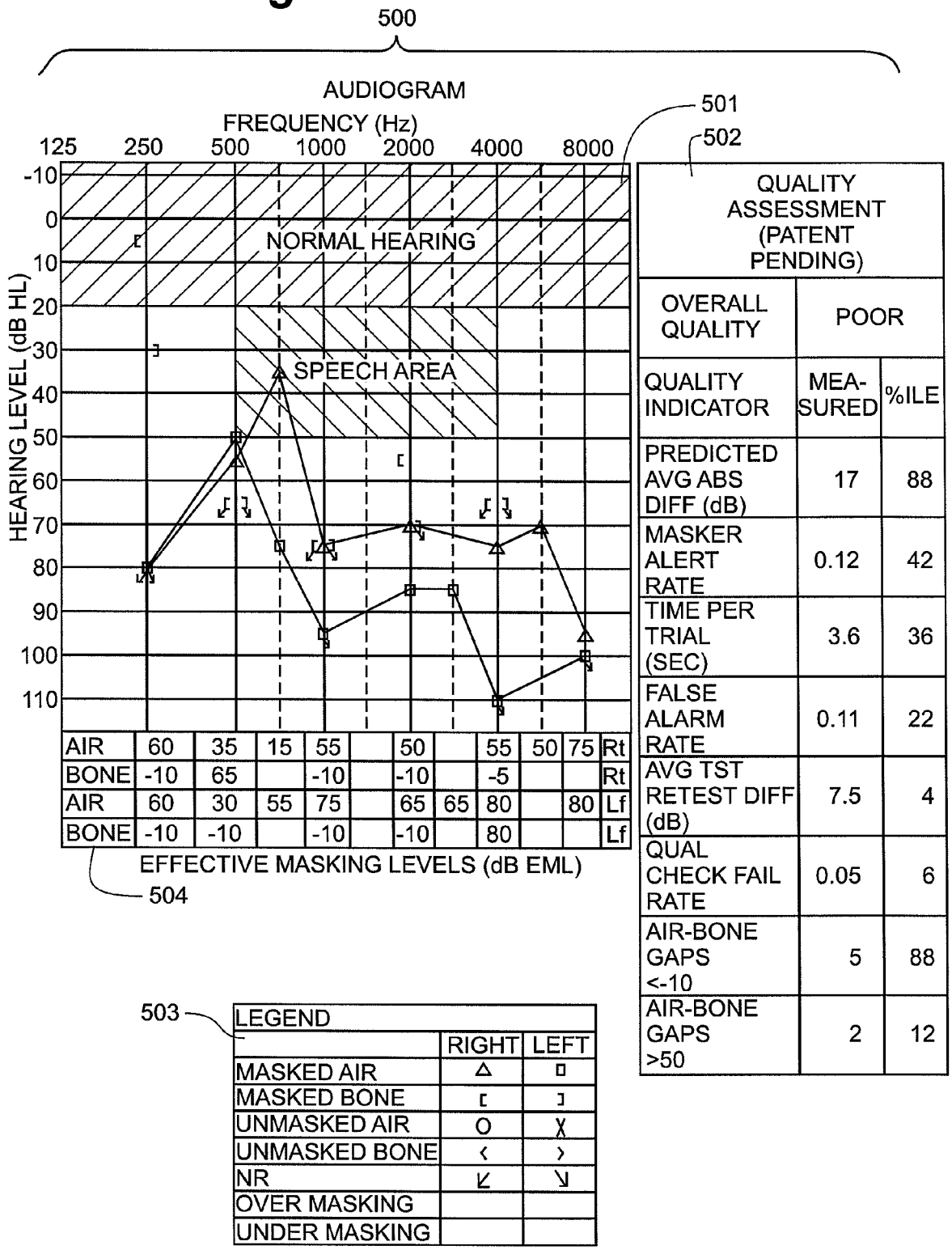
FIG. 12 is an illustration of a test diagnostic according to an embodiment of the invention.

Thus, the AMTAS procedure can be performed on any subject to obtain measurements for the psychometric quantity ($Q_m$) and also the quality indicators ($QI_n$). As illustrated in FIG. 12, the psychometric quantity measurements can be provided as an audiogram 501 on a test diagnostic 500. The quality indicator measurements ($QI_n$) can also be provided as raw measurements, as shown in the second column 502a of the quality assessment display 502 of the test diagnostic. Likewise, the subject's quality indicator measurements can each be compared to quality indicator measurements taken from a population group. For example, the subject's quality indicator measurements can be expressed as a percentile rank that compares with measurements from the population group, as shown in the third column 502b of the quality assessment display 502 of the test diagnostic.

An estimate of test accuracy QA can be obtained by the following previously derived formula:

$$QA=Q_t-Q_m=f(QI_n)=\Sigma(C \cdot QI)_n+K$$

where $Q_t$ is the measure of Q obtained by the test, $Q_m$ is the independent measure of Q that is obtained in the validation process, $QI_n$ are the measurements of the quality indicators, C is the coefficient for the quality indicator obtained from a multiple regression or other statistical method, and K is a constant also obtained from a multiple regression or other statistical method. This formula produces a calculation of estimated test accuracy (QA). The estimated test accuracy is also compared to the measured test accuracies in a population group. For example, with reference to the graph of FIG. 11, the QA values estimated by the formula and the measures of test accuracy for a population group can be plotted on a graph and the estimated QA can be placed into a category of "good", "fair" or "poor" depending on where that QA falls on the graph. FIG. 11 shows the relationship between the average absolute difference (measured accuracy) and the predicted absolute difference (calculated accuracy) for 123 patients with various degrees and types of hearing loss. The two dimensional space was subdivided into three regions representing "good", "fair", and "poor" accuracy. Of course, any mechanism of comparing QA to other measures in a population group can be used. Likewise, any number of data sets of measures from a population group can be obtained and the QA can be compared to any desired data set.

In some embodiments, data sets for several different population groups can be provided and the subject is associated with a particular group. For example, if the subject is a normal hearing male adult, he can then be associated with a population group for normal hearing adults. That particular group's data set can then be used to make the comparisons of QA. Once the QA has been placed into a category, this category can be displayed in the overall quality box 503 of the test diagnostic shown in FIG. 12. In the sample diagnostic shown in FIG. 12, the overall quality box displays a "poor" category. The test diagnostic 500 can also include a masking level display 504, which displays the masker level at threshold for each threshold result. Also, a legend 505 can also be provided on the test diagnostic, to aid an examiner or independent person interpreting the test results.

While a preferred embodiment of the present invention has been described, it should be understood that various changes, adaptations and modifications may be made therein without departing from the spirit of the invention and the scope of the appended claims.

What is claimed is:

1. A method for developing a predictive formula for calculating a quantitative measure of test accuracy, comprising:
   performing a behavioral test on a subject using a test system to measure a psychometric quantity;
   measuring the psychometric quantity to provide a test measurement of the psychometric quantity;
   measuring one or more quality indicators to provide one or more quality indicator measurements, the quality indicator being any variable that gives an indication of test accuracy;
   obtaining an independent measurement of the psychometric quantity for the subject, independent measurement being obtained separately from said behavioral test;
   calculating a difference between the test measurement and the independent measurement;
   determining a relationship between the quality indicator measurements and the difference between the test measurement and the independent measurement; and
   deriving a predictive formula based on the relationship, wherein the predictive formula can be used to calculate a quantitative measure of test accuracy in the behavioral test on future subjects.

2. The method of claim 1 wherein the performing a behavioral test comprises:
   providing stimuli to the subject; and
   receiving, from the subject, responses to the stimuli.

3. The method of claim 1 wherein the measuring one or more quality indicators comprises measuring quality indicators based upon variables seen when the stimuli is provided or when the responses are received.

4. The method of claim 1 wherein the obtaining an independent measurement comprises performing a method for measuring the psychometric quantity that is regarded as an accurate method for measuring that psychometric quantity.

5. The method of claim 4 wherein the obtaining an independent measurement comprises performing a standardized test method for measuring the psychometric quantity.

6. The method of claim 1 wherein the deriving a predictive formula comprises performing a multiple regression for the quality indicator measurements and the difference between the test measurement and the independent measurement.

7. The method of claim 6 wherein the predictive formula is $QA=Q_i-Q_m=f(QI_n)$.

8. The method of claim 1 wherein at least one of the quality indicators is a behavior.

9. The method of claim 8 wherein at least one of the quality indicators is a subject behavior.

10. The method of claim 1 wherein the steps of performing a behavioral test on a subject to measure a psychometric quantity is administered automatically and the step of obtaining an independent measurement of the psychometric quantity is administered manually.

11. The method of claim 1 wherein the behavioral test is a hearing test and the psychometric quantity is a frequency threshold.

12. The method of claim 11 wherein the one or more quality indicators include a masker alert rate, time per trial, average number of trials for a threshold, total elapsed time, false alarm rate, average test-retest difference, quality check fail rate, air-bone gap >50 dB and air-bone gap <−10 dB.

* * * * *

UNITED STATES PATENT AND TRADEMARK OFFICE
CERTIFICATE OF CORRECTION

| | | |
|---|---|---|
| PATENT NO. | : 7,704,216 B2 | Page 1 of 1 |
| APPLICATION NO. | : 11/210396 | |
| DATED | : April 27, 2010 | |
| INVENTOR(S) | : Robert H. Margolis | |

It is certified that error appears in the above-identified patent and that said Letters Patent is hereby corrected as shown below:

The following heading and paragraph should be inserted in column 1 after the title and before the heading "FIELD OF THE INVENTION":

--STATEMENT REGARDING FEDERALLY SPONSORED RESEARCH OR DEVELOPMENT

This invention was made with government support under one or more of grant no. R41 DC005110 and grant no. R42 DC005110, both awarded by the National Institute on Deafness and Other Communication Disorders, part of the National Institutes for Health. The Government has certain rights in the invention.--

Signed and Sealed this
Nineteenth Day of July, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,704,216 B2 | Page 1 of 1 |
| APPLICATION NO. | : 11/210396 | |
| DATED | : April 27, 2010 | |
| INVENTOR(S) | : Robert H. Margolis | |

It is certified that error appears in the above-identified patent and that said Letters Patent is hereby corrected as shown below:

The following paragraph should replace the paragraph following the heading "STATEMENT REGARDING FEDERALLY SPONSORED RESEARCH OR DEVELOPMENT" in column 1, line 4:

--This invention was made with government support under grant no. R41 DC005110 and grant no. R42 DC005110, both awarded by the National Institutes of Health. The Government has certain rights in the invention.--

Signed and Sealed this
Sixth Day of March, 2012

David J. Kappos
*Director of the United States Patent and Trademark Office*